(12) United States Patent
Austin et al.

(10) Patent No.: US 12,148,515 B2
(45) Date of Patent: *Nov. 19, 2024

(54) HEALTH CARE PRESCRIPTION SYNCHRONIZATION BETWEEN PATIENT AND HEALTH CARE PROVIDER

(71) Applicant: Smith & Nephew, Inc., Memphis, TN (US)

(72) Inventors: Gene E. Austin, Bartlett, TN (US); Johnny R. Mason, Olive Branch, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/222,580

(22) Filed: Jul. 17, 2023

(65) Prior Publication Data

US 2023/0386631 A1    Nov. 30, 2023

Related U.S. Application Data

(63) Continuation of application No. 17/541,893, filed on Dec. 3, 2021, now Pat. No. 11,728,019, which is a
(Continued)

(51) Int. Cl.
*A61B 17/66* (2006.01)
*G06F 3/04842* (2022.01)
(Continued)

(52) U.S. Cl.
CPC ......... *G16H 20/10* (2018.01); *G06F 3/04842* (2013.01); *G06F 3/0488* (2013.01);
(Continued)

(58) Field of Classification Search
CPC ............................. A61F 2/2846; A61B 17/66
(Continued)

(56) References Cited

U.S. PATENT DOCUMENTS 6,022,349 A   2/2000   McLeod et al.
6,371,123 B1  4/2002   Stark et al.
(Continued)

FOREIGN PATENT DOCUMENTS

CN   102883671 A   1/2013
JP   201366672 A   4/2013
(Continued)

OTHER PUBLICATIONS

European Patent Office, Summons to Attend Oral Proceedings Pursuant to Rule 115(1) EPC, dated Dec. 11, 2023, 11 pages.
(Continued)

*Primary Examiner* — Reginald R Reyes
(74) *Attorney, Agent, or Firm* — KDW Firm PLLC

(57) ABSTRACT

Methods and devices for implementation of a health care prescription. Some devices may dynamically monitor information from a patient device. Some embodiments may dynamically provide instructions to patient devices to treat and for treating patients through the use of medical devices based on the information from a patient device. Some embodiments treat musculoskeletal conditions by providing for alignment of bones by use of bone alignment devices in accordance with instructions provided through a prescription. Other embodiments may facilitate or provide revised prescriptions in response to treatment conditions. Embodiments may also provide effective ways of communicating prescription and compliance information between patients and health care providers.

21 Claims, 12 Drawing Sheets

Related U.S. Application Data continuation of application No. 16/937,130, filed on Jul. 23, 2020, now Pat. No. 11,600,368, which is a continuation of application No. 14/891,540, filed as application No. PCT/US2014/037983 on May 14, 2014, now abandoned.

(60) Provisional application No. 61/861,538, filed on Aug. 2, 2013, provisional application No. 61/822,993, filed on May 14, 2013.

(51) Int. Cl.
| | |
|---|---|
| G06F 3/0488 | (2022.01) |
| G16H 20/10 | (2018.01) |
| G16H 20/30 | (2018.01) |
| G16H 30/20 | (2018.01) |
| G16H 40/67 | (2018.01) |
| G16H 15/00 | (2018.01) |

(52) U.S. Cl.
CPC ............. *G16H 20/30* (2018.01); *G16H 30/20* (2018.01); *G16H 40/67* (2018.01); *G16H 15/00* (2018.01)

(58) Field of Classification Search
USPC ....................................................... 623/23.51
See application file for complete search history.

(56) References Cited

U.S. PATENT DOCUMENTS

| | | |
|---|---|---|
| 7,668,731 B2 | 2/2010 | Martucci et al. |
| 8,032,397 B2 | 10/2011 | Lawless |
| 8,864,750 B2 | 10/2014 | Ross et al. |
| 2003/0189732 A1 | 10/2003 | Bean et al. |
| 2003/0191466 A1* | 10/2003 | Austin .................. A61B 17/62 |
| | | 606/54 |
| 2008/0051779 A1 | 2/2008 | Mackenzie et al. |
| 2012/0053956 A1 | 3/2012 | Martin et al. |
| 2012/0101840 A1 | 4/2012 | Choi |
| 2012/0296666 A1 | 11/2012 | Hanina et al. |
| 2012/0303388 A1 | 11/2012 | Vishnubhatla et al. |
| 2013/0138017 A1 | 5/2013 | Jundt et al. |
| 2014/0031642 A1 | 1/2014 | Kimchy et al. |
| 2014/0225999 A1 | 8/2014 | Bracke et al. |
| 2014/0236153 A1* | 8/2014 | Edelhauser ............ A61B 17/62 |
| | | 606/56 |
| 2014/0316421 A1 | 10/2014 | Sanders |

FOREIGN PATENT DOCUMENTS

| | | |
|---|---|---|
| JP | 201384082 A | 5/2013 |
| JP | 6022349 B2 * | 11/2016 |
| WO | 2009105479 A1 | 8/2009 |
| WO | 2011146703 A1 | 11/2011 |

OTHER PUBLICATIONS

Examination Report No. 1 for Australian Patent Application No. 2014265471, mailed Feb. 15, 2019.
Decision of Rejection for Japanese Patent application No. 2016514057, mailed Mar. 4, 2019.
Communication to pursuant to Article 94(3) EPC for European Patent Application No. 14798173.2, mailed Mar. 21, 2019.
Third Office Action in the CN Application No. 201480040097.7 mailed Jan. 3, 2019.
Second Office Action in the CN Application No. 201480040097.7 mailed Jun. 5, 2018.
European Examination Report; European Patent Office; European Patent Application No. 14798173.2; May 4, 2017; 15 pages.
Chinese Office Action (First); Chinese Patent Office; Chinese Patent Application No. 201480040097.7; Aug. 2, 2017; 26 pages.
Notice of Reasons for Rejection in the JP Application No. 2016-514057 mailed Apr. 23, 2018.
International Search Report and Written Opinion, International Application No. PCT/US14/37983, Dec. 10, 2014, 10 pages.
Examination Report for Indian Patent Application No. 7017/CHENP/2015, mailed May 15, 2020.
Notice of Reasons for Rejection for Japanese Application No. JP2019-125333, on Oct. 26, 2020, original and translated documents, 13 pages.
Communication pursuant to Article 94(3) EPC for Application No. 14798173.2, dated Mar. 2, 2021, 6 pages.
Notice of Reexamination for Chinese Patent application No. 201480040097.7, dated May 18, 2021, 23 pages [original and translation].

\* cited by examiner

FIG. 4

| | | | | | | | | |
|---|---|---|---|---|---|---|---|---|
| Cases | Case 1 | | | | Resources | Account | | Contact Us |

Save  Save As  Close                                    Create New Case

1. Case Info > 2. Deformity > 3. Frame > 4. Mount > 5. Strut Settings > 6. Duration/SAR > 7. Prescription

▶ Prescription:                                     Case Case 1

Your Contact for this Case: edit | Your Notes for this Prescription: edit
                                   Click to edit Prescription | Report   Prescription Start Date: 04/01/2013

Spatial Frame Prescription                          Printable PDF Version
The Prescription is intended to be given to the Patient or the Patient's Caretaker.   opens in new window

| Date | Day | Strut 1 | Strut 2 | Strut 3 | Strut 4 | Strut 5 | Strut 6 | Status |
|---|---|---|---|---|---|---|---|---|
| 04/01/13 | 0 | 191 | 150 | 194 | 200 | 180 | 150 | Done |
| 04/02/13 | 1 | 190 | 150 | 193 | 199 | 179 | 151 | Done |
| 04/03/13 | 2 | 189 | 150 | 191 | 197 | 179 | 151 | Done |
| 04/04/13 | 3 | 188 | 151 | 190 | 196 | 178 | 152 | Done |
| 04/05/13 | 4 | 187 | 151 | 188 | 195 | 177 | 152 | Done |
| 04/06/13 | 5 | 186 | 151 | 187 | 193 | 177 | 153 | Done |
| 04/07/13 | 6 | 185 | 151 | 186 | 192 | 176 | 153 | Done |
| 04/08/13 | 7 | 184 | 151 | 184 | 191 | 176 | 154 | Done |
| 04/09/13 | 8 | 183 | 152 | 183 | 189 | 175 | 154 | Done |
| 04/10/13 | 9 | 182 | 152 | 181 | 188 | 174 | 155 | Done |
| 04/11/13 | 10 | 181 | 152 | 180 | 187 | 174 | 156 | Done |
| 04/12/13 | 11 | 180 | 152 | 179 | 186 | 173 | 156 | Done |
| 04/13/13 | 12 | 179 | 152 | 177 | 184 | 172 | 157 | |
| 04/14/13 | 13 | 178 | 153 | 176 | 183 | 172 | 157 | |
| 04/15/13 | 14 | 177 | 153 | 174 | 182 | 171 | 158 | |
| 04/16/13 | 15 | 176 | 153 | 173 | 180 | 170 | 158 | |
| 04/17/13 | 16 | 175 | 153 | 172 | 179 | 170 | 159 | |
| 04/18/13 | 17 | 174 | 153 | 170 | 178 | 169 | 160 | |
| 04/19/13 | 18 | 173 | 154 | 169 | 176 | 168 | 160 | |
| 04/20/13 | 19 | 172 | 154 | 167 | 175 | 168 | 161 | |
| 04/21/13 | 20 | 171 | 154 | 166 | 174 | 167 | 161 | |
| 04/22/13 | 21 | 170 | 154 | 165 | 172 | 167 | 162 | |
| 04/23/13 | 22 | 169 | 154 | 163 | 171 | 166 | 162 | |
| 04/24/13 | 23 | 168 | 155 | 162 | 170 | 165 | 163 | |
| 04/25/13 | 24 | 167 | 155 | 160 | 169 | 165 | 163 | |
| 04/26/13 | 25 | 166 | 155 | 159 | 167 | 164 | 164 | |

Strut Change-Outs

| Change-Out | Strut | Overlap Interval | | Strut Change | |
|---|---|---|---|---|---|
| | | First Day | Last Day | From | To |
| | | No strut change-outs are required. | | | |

◀ Go Back to Step 4                      Continue to Step 6 ▶

Help

The Prescription shows the schedule the patient is expected to follow for strut adjustments. The colored areas indicate a strut change out.

You may edit your Contact Info and Case Notes. Here you may want to put your clinic contact information as well as your suggestions for strut adjustments, pin and frame care as well as patients next appointment information.

On the Report tab you will find all of your deformity and mounting parameters along with the frame construct and Prescription. It is advised to print and place in patient's permanent record..

FIG. 7

| | | | | | Welcome | | Logout | |
|---|---|---|---|---|---|---|---|---|
| Cases | Case 1 | | | | | Resources | Account | Contact Us |

Save   Save As   Close                                                                    Create New Case 1. Case Info  >  2. Deformity  >  3. Frame  >  4. Mount  >  5. Strut Settings  >  6. Duration/SAR  >  7. Prescription

▶ Prescription:    Case Case 1 - Day 12 Prescription Change

Your Contact for this Case: edit    Your Notes for this Prescription: edit
                                     Click to edit Prescription | Report    Prescription Start Date: 04/13/2013

Spatial Frame Prescription    Printable PDF Version
The Prescription is intended to be given to the Patient or the Patient's Caretaker.    opens in new window

| Date | Day | Strut 1 | Strut 2 | Strut 3 | Strut 4 | Strut 5 | Strut 6 | Status |
|---|---|---|---|---|---|---|---|---|
| 04/13/13 | 0 | 179 | 152 | 177 | 184 | 172 | 157 | |
| 04/14/13 | 1 | 179 | 152 | 176 | 183 | 172 | 158 | |
| 04/15/13 | 2 | 178 | 152 | 175 | 182 | 171 | 158 | |
| 04/16/13 | 3 | 178 | 152 | 175 | 181 | 171 | 159 | |
| 04/17/13 | 4 | 178 | 153 | 174 | 180 | 171 | 159 | |
| 04/18/13 | 5 | 177 | 153 | 173 | 179 | 170 | 160 | |
| 04/19/13 | 6 | 177 | 153 | 172 | 178 | 170 | 160 | |
| 04/20/13 | 7 | 176 | 153 | 171 | 177 | 170 | 161 | |
| 04/21/13 | 8 | 176 | 153 | 171 | 175 | 169 | 161 | |
| 04/22/13 | 9 | 176 | 153 | 170 | 174 | 169 | 162 | |
| 04/23/13 | 10 | 176 | 153 | 169 | 173 | 169 | 162 | |
| 04/24/13 | 11 | 175 | 153 | 168 | 172 | 168 | 163 | |
| 04/25/13 | 12 | 175 | 154 | 167 | 171 | 168 | 163 | |
| 04/26/13 | 13 | 175 | 154 | 167 | 170 | 168 | 164 | |
| 04/27/13 | 14 | 174 | 154 | 166 | 169 | 167 | 164 | |
| 04/28/13 | 15 | 174 | 154 | 166 | 168 | 167 | 165 | |

Strut Change-Outs

| Change-Out | Strut | Overlap Interval | | Strut Change | |
|---|---|---|---|---|---|
| | | First Day | Last Day | From | To |
| | | No strut change-outs are required. | | | |

◀ Go Back to Step 6                               Save & Go To My Cases ✓

Help

The Prescription shows the schedule the patient is expected to follow for strut adjustments. The colored areas indicate a strut change out.

You may edit your Contact Info and Case Notes. Here you may want to put your clinic contact information as well as your suggestions for strut adjustments, pin and frame care as well as patients next appointment information.

On the Report tab you will find all of your deformity and mounting parameters along with the frame construct and Prescription. It is advised to print and place in patient's permanent record..

FIG. 9

HEALTH CARE PRESCRIPTION SYNCHRONIZATION BETWEEN PATIENT AND HEALTH CARE PROVIDER

CROSS-REFERENCE TO RELATED APPLICATIONS

This application is a continuation of pending U.S. patent application Ser. No. 17/541,893, filed Dec. 3, 2021, which application is a continuation of U.S. patent application Ser. No. 16/937,130, filed Jul. 23, 2020, now U.S. Pat. No. 11,600,368, which application is a continuation of U.S. patent application Ser. No. 14/891,540, filed Nov. 16, 2015, which application is a U.S. National Stage entry of International Application No. PCT/US2014/037983, filed May 14, 2014, which claims the benefit of U.S. Provisional Application No. 61/822,993, filed May 14, 2013, and U.S. Provisional Application No. 61/861,538, filed Aug. 2, 2013. The disclosures of each of these applications are incorporated by reference in their entirety.

BRIEF DESCRIPTION OF THE DRAWINGS

The accompanying drawings are incorporated in and form a part of the specification, illustrate the embodiments of the invention, and together with the written description serve to explain the principles, characteristics, and features of the invention. In the drawings:

FIG. 4 is a screenshot of an embodiment of a portion of a system used for aligning one or more bones of a patient.

FIG. 7 is a screenshot of an embodiment of a portion of a system used for aligning one or more bones of a patient illustrating a revised prescription.

FIG. 9 is a screenshot of an embodiment of a portion of a system used for aligning one or more bones of a patient.

DETAILED DESCRIPTION OF THE EMBODIMENTS

The following descriptions of the depicted embodiments are merely exemplary in nature and are in no way intended to limit the invention, its application, or uses.

Figure 1:
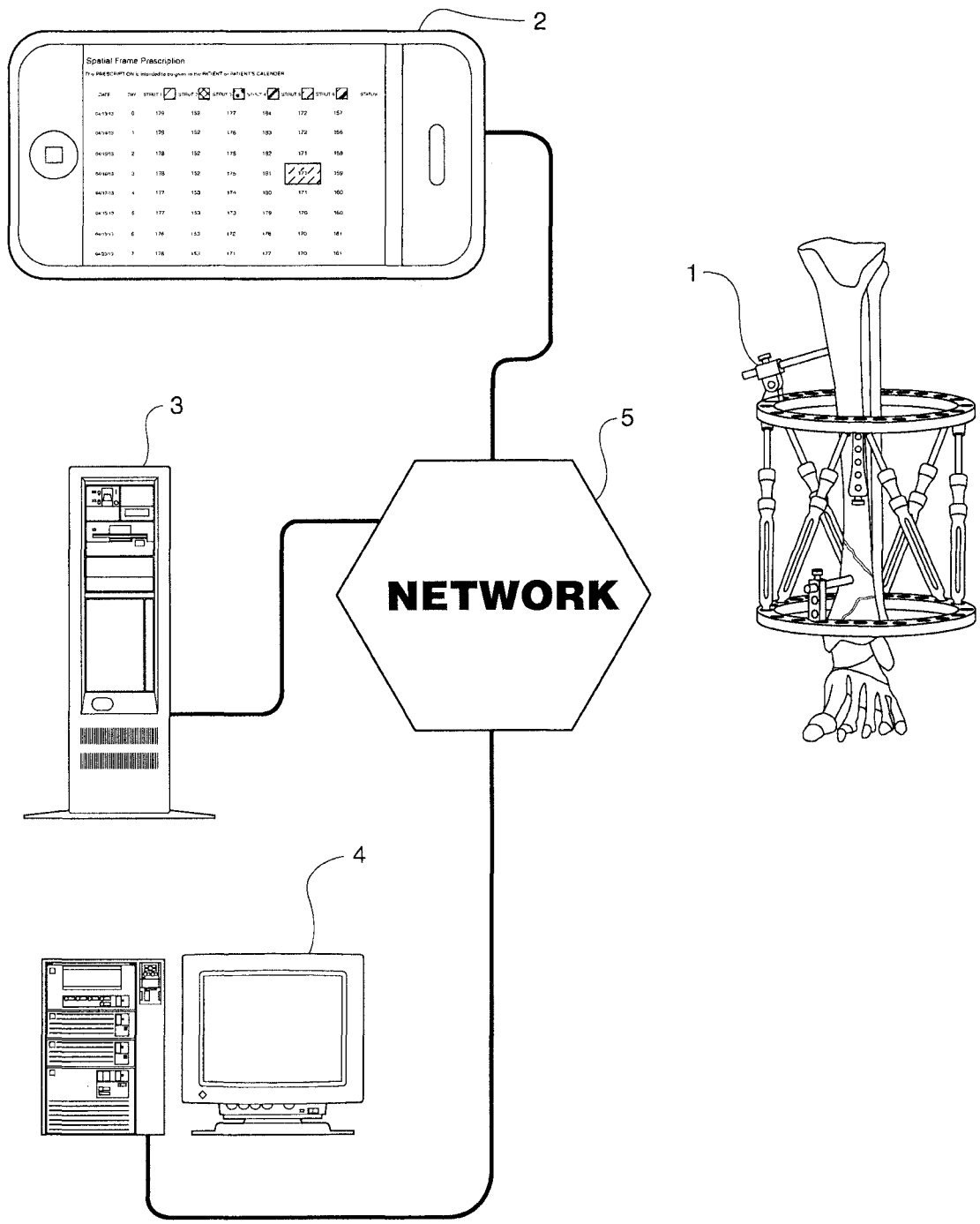
FIG. 1 is a system drawing of an embodiment of a system for treating a patient.

A system for treating a patient is illustrated in FIG. 1. The particular system illustrated includes a bone alignment device 1 configured to be coupled to a patient, a patient device 2 connected to a network 5, a server computer 3 connected to the network 5, and a health care provider (HCP) device 4 connected to the network 5. The illustrated bone alignment device 1 is a six-axis external fixator. In other embodiments, a bone alignment device may be any device capable of coupling to two or more bones or pieces of bone and moving or aligning the bones or pieces of bone relative to one another. In yet other embodiments, a device for use in a system within the scope of embodiments of the invention may be any type of medical device for which a set of instructions to be accomplished over a predetermined period of time, or prescription, of any type is useful for the operation of the device.

The patient device 2 illustrated is a handheld cellular device. In other embodiments, a patient device may be any brand or type of electronic device capable of executing a computer program and outputting results to a patient. For example, and without limitation, a patient device may be a smartphone, a tablet computer, or any other type of electronic device capable of providing one or both of input and output of information. In some embodiments, a patient device is a patient owned device. In some embodiments, a patient device is a handheld device. Such a device may provide ready access for input and output for a patient to whom a medical device such as the bone alignment device 1 is coupled. A patient device such as the patient device 2 may be distinguishable from an HCP device such as the HCP device 4 at least in that a patient device would not necessarily require permission or interaction from an HCP in order for a patient to transmit or receive information regarding the patient's treatment through the patient device. A patient device such as the patient device 2 may be connected to the network 5 by any effective mechanism. For example, and without limitation, the connection may be by wired or wireless connection through any number of routers and switches. Data may be transmitted by any effective data transmission protocol. Any patient device of the system may include integrated or separate computer readable media containing instructions to be executed by the patient device. For example, and without limitation, computer readable media may be any media integrated into the patient device such as a hard disc drive, RAM, or non-volatile flash memory. Such computer readable media, once loaded into the patient device as defined herein, may be integrated and non-transitory data storage media. Similarly, computer readable media may be generally separable from the patient device, such as a flash drive, external hard disc drive, CD, or DVD that is readable directly by the patient device or in combination with a component connectable to the patient device.

The network 5 may be one or more interconnected networks, whether dedicated or distributed. Non-limiting examples include intranets, the Internet, cellular data communications networks, and switched telephonic networks or systems. Connections to the network 5 may be continuous or may be intermittent, only providing for a connection when requested by a sending or receiving client.

The server computer 3 is shown connected to the network 5 in FIG. 1. The server computer 3 may be a single computing device in some embodiments or may itself be a collection of two or more computing devices that collectively function to process data as described herein. The server computer 3, or any of its two or more computing devices, if applicable, may connect to the network 5 through one or both of firewall and web server software and may include one or more databases. If two or more computing devices or programs are used, the devices may interconnect through a back-end server application or may connect through separate connections to the network 5. The server computer 3 or any component server device of the system may include integrated or separate computer readable media containing instructions to be executed by the server computer. For example, and without limitation, computer readable media may be any media integrated into the server computer such as a hard disc drive, RAM, or non-volatile flash memory. Such computer readable media, once loaded into the server computer as defined herein, may be integrated and non-transitory data storage media. In some embodiments, a server computer 3 may be a storage location for information that will be eventually used by any or all of the patient device 2, the server computer 3, and the HCP device 4. When stored on the server computer 3, memory devices of the server computer 3, as defined herein, provide non-transitory data storage and are computer readable media containing instructions. Similarly, computer readable media may be generally separable from the server computer, such as a flash drive, external hard disc drive, CD, or DVD that is readable directly by the server computer or in combination with a component connectable to the server computer 3.

The HCP device 4 is shown connected to the network 5. The HCP device 4 illustrated is a desktop personal computer. In other embodiments, an HCP device may be any brand or type of electronic device capable of executing a computer program and receiving inputs from or outputting information to an HCP. For example, and without limitation, an HCP device may be a smartphone, a tablet computer, or any other type of electronic device capable of providing one or both of input and output of information. Such a device may provide an interface for data input, compliance monitoring, prescription modification, and communication with a patient, another HCP, or a device or system manufacturer. An HCP device such as the HCP device 4 may be connected to the network 5 by any effective mechanism. For example, and without limitation, the connection may be by wired or wireless connection through any number of routers and switches. Data may be transmitted by any effective data transmission protocol. Any HCP device of the system may include integrated or separate computer readable media containing instructions to be executed by the HCP device. For example, and without limitation, computer readable media may be any media integrated into the HCP device such as a hard disc drive, RAM, or non-volatile flash memory. Such computer readable media once loaded into the HCP device as defined herein may be integrated and non-transitory data storage media. Similarly, computer readable media may be generally separable from the HCP device, such as a flash drive, external hard disc drive, CD, or DVD that is readable directly by the HCP device or in combination with a component connectable to the HCP device.

Figure 2:
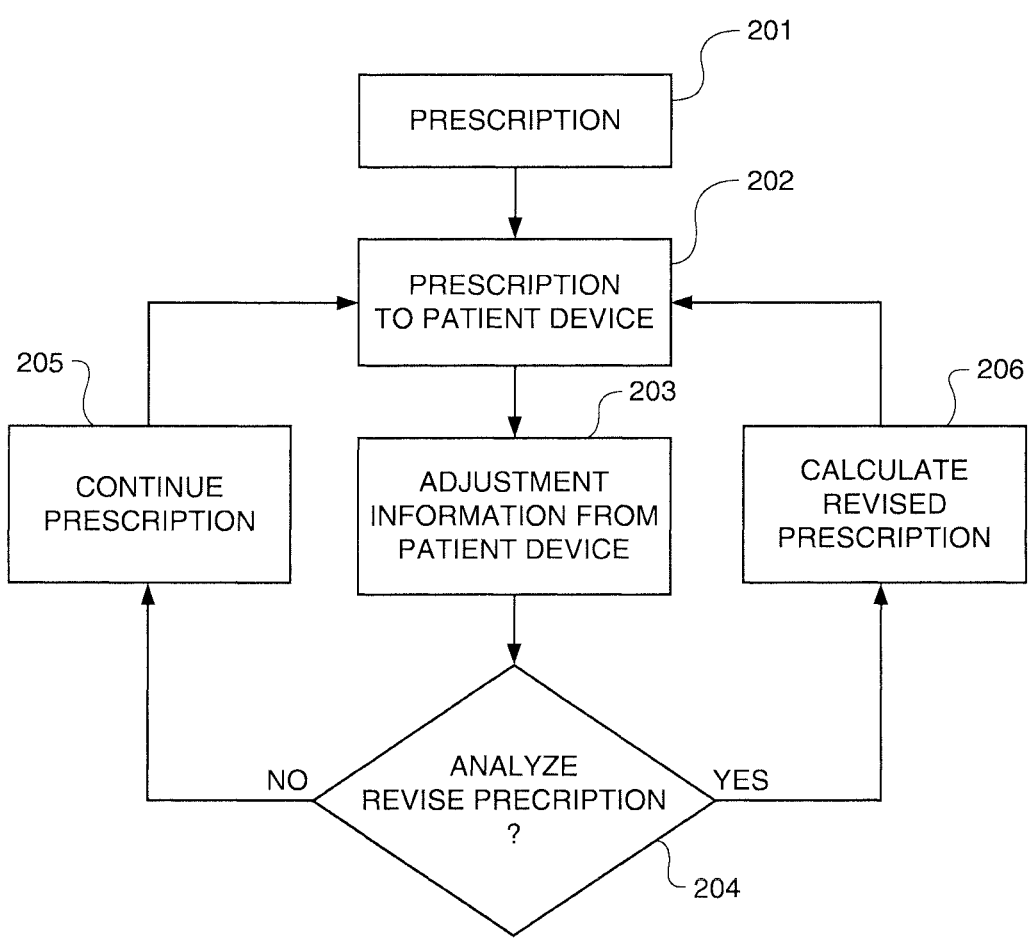
FIG. 2 is a flowchart depicting an embodiment of a method of dynamically providing instructions to transform a bone alignment device.
Figure 3:
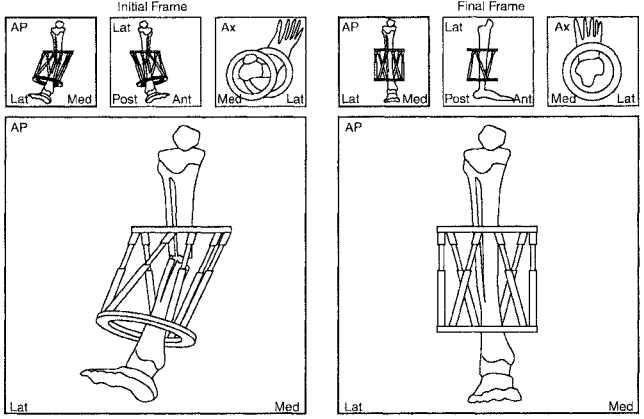
FIG. 3 is a screenshot of a prior art system used for aligning one or more bones of a patient.

A flowchart depicting an embodiment of a method of dynamically providing instructions to transform a bone alignment device is shown in FIG. 2. Block 201 illustrates that a prescription is generated by or at the direction of an HCP. Generation of a prescription for the bone alignment device 1, for example, may be accomplished with the assistance of software provided through www.spatialframe.com, as described herein. Following input of deformity measurement information, an initial frame configuration, and distraction or correction rate information, software that is part of the website in this example generates a prescription, subject to the review and approval of an HCP. In this embodiment, the prescription is a set of instructions to be accomplished over a predetermined period of time. Depictions of the strut settings and mounting information resulting from input of deformity and frame configuration information is shown in FIG. 3. The information and function illustrated in FIG. 3 is the same for the prior art system and the system of the present application.

Block 202 of FIG. 2 illustrates communicating a set of instructions to be accomplished over a predetermined period of time to a patient device to achieve alignment of one or more bones by adjustment of a bone alignment device coupled to a patient. As used herein, the term predetermined period of time means a period of time that is initially set to accomplish a correction under the initial prescription. If a prescription is revised, a time to complete the prescription may also be revised, thereby revising the original period of time and setting a revised predetermined period of time. In the example of FIG. 1, the instructions, or prescription, may be communicated from the server computer 3 over the network 5 to the patient device 2.

Figure 5:
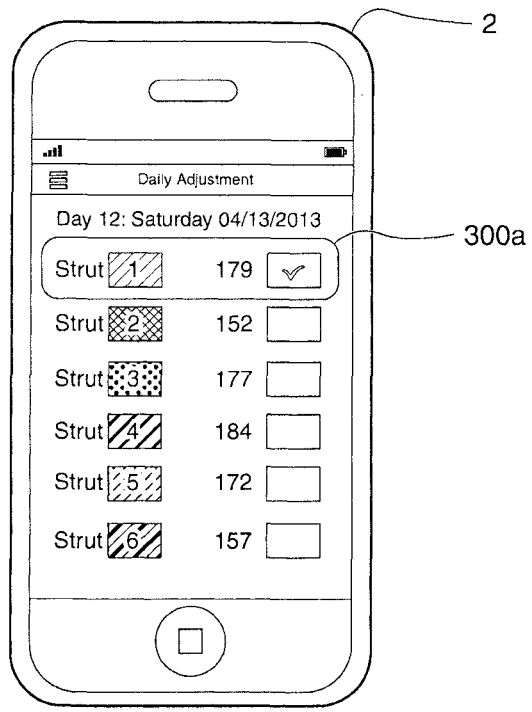
FIG. 5 is a depiction of a patient device displaying daily adjustments prescribed for a bone alignment device configured to be coupled to a patient.
Figure 6:
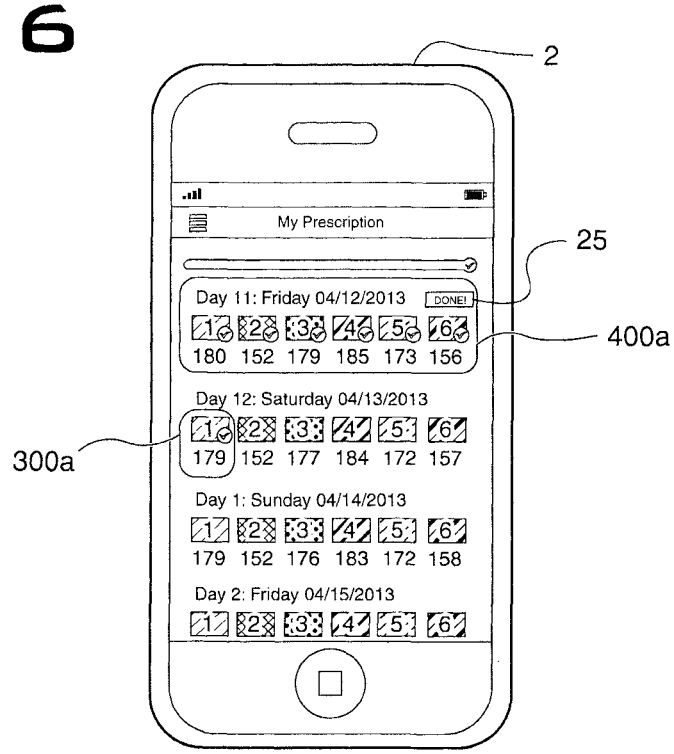
FIG. 6 is a depiction of a patient device displaying multiple days of a prescription for a bone alignment device configured to be coupled to a patient.

Following communication of a prescription to a patient device, actions may be accomplished on the bone alignment device and a record of those actions conveyed to the patient device. Actions may be taken by a patient to whom the bone alignment device is coupled, by an HCP, or by any other designee capable of performing the actions. Actions may be performed manually or may be executed automatically on a time schedule or in response to some other initiating activity. Recording of actions accomplished on the bone alignment device 1 is illustrated in FIGS. 4-6. A prescription for adjustment of struts 1-6 of a bone alignment device is illustrated in FIG. 4. The far right-hand column of the prescription shows a Status column which is designated "Done" for the first 11 days of the prescription. FIGS. 5 and 6 show an interface on the patient device 2 where actions that have been accomplished are recorded. In particular, FIG. 5 illustrates a daily adjustment input screen where actions taken on the bone alignment device may be recorded. In this example, Strut 1 has been recorded as being adjusted to 179 mm, as indicated by the checkmark on the right side of the Strut 1 row. A depiction of a patient's prescription is illustrated in FIG. 6 in sync with the daily adjustments shown in FIG. 5. An indication that daily prescription actions have been completed is illustrated in FIG. 6 with regard to day 11 by illumination of a "Done" tag 25. In addition to information about adjustments of parts of the bone alignment device, information that may be recorded on a patient device includes but is not limited to, one or more pictures of the bone alignment device and patient, readings of forces being transmitted through parts of the bone alignment device, identification information associated with the bone alignment device, and subjective information from a patient to whom the bone alignment device is coupled, such as but not limited to, pain experienced by the patient. Any one or all of these types of information may be recorded on a patient device.

As illustrated in FIG. 2, block 203, some method embodiments include receiving information from the patient device 2 regarding one or more adjustments made to the bone alignment device 1. In some embodiments, receiving information from the patient device 2 includes receiving information input into the patient device 2 by the patient to whom the bone device is coupled. In some embodiments, receiving information from the patient device 2 includes receiving a notification that the prescribed adjustments for a particular time period have been completed. Receiving information may also include receiving an indication that one or more adjustments have not been made to the bone alignment device 1 in accordance with a set of instructions to be accomplished over a predetermined period of time. In some embodiments, receiving information from the patient device 2 includes receiving information transmitted as a result of a transmission initiated from the patient device 2. For example, a patient device 2 may automatically push data to a server computer 3 when a particular day's information is input into the patient device 2. As shown in FIG. 6 with regard to day 11 for example, when the adjustment information for day 11 was completed, the "Done" tag 25 was generated and a "Done" indication was placed in the Status column of the website, as illustrated in FIG. 4.

In some embodiments, a server computer such as the server computer 3 may be configured to receive information from the patient device 2 and monitor for compliance with the prescription embodied in the set of instructions to be accomplished over a predetermined period of time. The server computer 3 may also generate one or more notices if information is not received from the patient device 2 that confirms compliance with the prescription. Such a notice may be transmitted, without limitation, to one or more of the patient device 2, the HCP device 4, e-mail accounts, phone numbers by one or more of voice and text message, and any other effective method of communication.

Information received from a patient device may include information about adjustments made to parts of the bone alignment device, one or more pictures of the bone alignment device and patient, readings of forces being transmitted through parts of the bone alignment device, identification information associated with the bone alignment device, and subjective information from a patient to whom the bone alignment device is coupled, such as but not limited to, pain experienced by the patient.

As shown in decision block 204 of FIG. 2, information received from a patient device requires analysis in some embodiments of the invention. The conclusion to be reached based on information received from a patient device is whether or not a prescription should be revised. Some non-limiting examples of when a prescription should be revised are listed below. If a bone align device has not been adjusted properly, either by mistakes made during adjustment or by noncompliance, then a revised prescription may be necessary to return a patient to a set of instructions that will result in a proper alignment. If a bone alignment device has shifted in relation to a patient's bone or the mounting of the device was originally improper, then a revised prescription may be necessary. If a patient is experiencing an intolerable or unusual amount of pain, then a revised prescription with a slower rate of correction may be necessary. System software may include an indicator selectable on a patient device for a patient to request a change to a prescription. Depending on the reason a prescription change is being requested, an HCP may be able to revise a prescription and provide the revised prescription to a patient device based on information received through the patient device and without physically examining the patient.

In an embodiment where a bone alignment device may also be used as part of a device to monitor the healing of a bone to which the bone alignment device is attached, the bone alignment device may include struts or other components that are capable of sensing forces that are being transmitted through the bone alignment device components. For example, where a bone is being lengthened, the percentage of force being transmitted through the healing bone compared with the percentage of force being transmitted through the bone alignment device may provide an HCP with information regarding when to continue the lengthening process of the bone.

One or more pictures received from a patient device may be analyzed alone or in combination with information about adjustments of parts of the bone alignment device to determine if a bone alignment device is being adjusted in accordance with a prescription. Such pictures may be taken with the patient device or uploaded to a patient device before analysis of information is conducted. Pictures may be taken from perspectives specified by software controlling the system. For example, highlighting may be superimposed on the camera screen of a patient device to instruct a user from which angle and at what distance to take a picture.

In some embodiments, the patient device may be capable of displaying an image of the bone alignment device at one or more stages of adjustment to illustrate to a patient how a bone alignment device should appear at each stage of adjustment, respectively. Some of these embodiments may also include the capability to display a graphical representation of the patient's anatomy to which the bone alignment device is coupled in relation to the bone alignment device as it should appear at each stage of adjustment, respectively.

If the answer resulting from analysis conducted at the juncture of decision box 204 shown in FIG. 2 is that no revised prescription should be issued, then as depicted in block 205, the original prescription should be continued. If, however, the answer resulting from analysis conducted is that the prescription should be revised, then as depicted in block 206, a revised prescription must be calculated. A revised prescription may include a revised set of instructions to be accomplished over a predetermined period of time to achieve alignment of one or more bones by adjustment of the bone alignment device coupled to the patient based on information received. The decision to calculate a revised prescription may be based on one or both of information received from the patient device and the discretion of a treating HCP. If a revised prescription is to be implemented, the original prescription must be terminated in favor of the revised prescription. Communication of a revised set of instructions to the patient device to enable transformation of the bone alignment device in accordance with the revised set of instructions is illustrated in FIG. 2 by an arrow from block 206 to block 204.

Implementation of an example revised prescription is illustrated in FIGS. 4-7. As noted above, a prescription for adjustment of struts 1-6 of a bone alignment device is illustrated in FIG. 4. The prescription illustrated is for a 25-day correction of a mid-shaft fracture of the right lower leg of a patient, similar to the case described in FIG. 3. As noted in the far right-hand column of the prescription, the status for the first 11 days of the prescription is "Done". On day 12 (e.g., Apr. 13, 2013), after adjusting Strut 1, as shown in FIGS. 5 and 6, the prescription was stopped. The stoppage could have been for any practical reason, but for this example, it may be assumed that the patient was experiencing an unusual amount of pain with the correction. An indication of excess pain was input into the patient device 2 and then received from the patient device 2 by the server computer 3. The server computer 3 analyzed the information received and notified the HCP through the HCP device 4.

The HCP, through the HCP device 4 authorized a revision of the rate of correction. The maximum safe distraction rate was changed from 1.5 mm/day to 1.0 mm/day. A revised prescription was calculated by the server computer 3 to be accomplished over a revised predetermined period of time to achieve alignment. The revised prescription is illustrated in FIG. 7. Day 0 of the revised prescription is Day 12 of the original prescription (e.g., Apr. 13, 2013) and the prescription time has been extended in total by two days. The revised prescription is also illustrated in FIG. 6 where Days 1 and 2 of the revised prescription are shown appended after Day 12 of the original prescription. Note that the distraction rate could have been lowered more drastically to increase the time of the revised prescription even further. Additionally, adjustments could have been stopped for a period of time and then restarted when pain had reduced acceptably. For example, the prescription could have been stopped at its partially adjusted state on Day 12 (see FIG. 5 with only Strut 1 adjusted), and a revised prescription could have been started from that point with a Day 0 several days later, wherein the revised Day 0 started with the strut settings of the partially adjusted original Day 12.

Continuing with the example case, the revised prescription may be communicated to the patient device to enable transformation of the bone alignment device in accordance with the revised prescription. A patient or any capable person or machine with access to the information provided on the patient device could then make the adjustments to the bone alignment device in accordance with the revised prescription.

Some methods may also include placing a unique identifier on a bone alignment device such that when a unique identifier is read or input into the patient device, the patient device automatically logs into a server computer configured to receive information from the patient device. Some similar embodiments may include instructions on the server computer that compare the information received from the patient device regarding adjustments made to the bone alignment device to information regarding adjustment scheduled to be performed to carry out the set of instructions to be accomplished over a predetermined period of time. Such instructions and functionality may assist an HCP with monitoring patient compliance with prescribe adjustments. Some similar embodiments may also include instructions to compare the information received from the patient device regarding identity and usage to registered identity and usage information. In circumstances where identity or usage information do not match registered identity and usage information, then the server computer may generate and send notices. This information may be useful in identifying improper reuse of a single use prescription device. Notices may be sent to one or more of the server computer, the software owner, and the HCP.

In some embodiments, information received from the patient device may be used to schedule clinical or follow-up visits for patients to whom a bone alignment device is coupled. Such scheduling may be done on a routine basis, may be a result of receiving data outside of certain parameters, or may be in response to particular messages received from the patient device.

An embodiment of the invention is a method means of changing a prescription for a bone alignment device comprising communicating a prescribed set of instructions to be accomplished over a predetermined period of time to a patient device to achieve alignment of one or more bones by adjustment of the bone alignment device and receiving information from the patient device regarding one or more adjustments made to the bone alignment device. Such a method may also include a step for analyzing the information received and a step for calculating a revised set of instructions to be accomplished over a predetermined period of time to achieve alignment of the one or more bones and all equivalents of these steps disclosed herein. Such a method may also include communicating the revised set of instructions to the patient device to enable a transformation of the bone alignment device in accordance with the revised set of instructions. Some embodiments of such a method may also include a step for adjusting the bone alignment device in accordance with the revised set of instructions. In various embodiments, adjusting the bone alignment device may include one or more of displaying instructions for adjustment, physically adjusting one or more struts, and providing signals to mechanized struts instructing the mechanized struts to adjust.

Another embodiment of the invention is a kit for use in treating a patient in accordance with a set of instructions to be accomplished over a predetermined period of time, or in other words, a prescription. Such a kit may be offered by a medical device manufacturer that may sell or other make available a bone alignment device and one or more computer readable media containing programs to be used to determine and revise prescriptions related to the use of the bone alignment device. A manufacturer or distributor may package the kit with a bone alignment device separate from the one or more computer readable media, or may package all elements together. The computer readable media, as detailed more specifically above, may be offered as media alone or may be integral with one or more of the computer devices of a system for treating a patient. The computer readable media of some embodiments is non-transitory data storage media, regardless of on which computer device instructions stored on the media are ultimately executed. For example, and without limitation, a kit may be offered that includes a bone alignment device and one or more media such as a DVD, CD, or flash memory, which include respectively or in combination the instructions of the first and second readable media described herein. In another non-limiting example, a kit may include a bone alignment device and a server computer on which one or both of the first and second readable media are stored. Although the server computer may not execute instructions that are configured to be programmed into a patient device, the server computer does constitute computer readable media by virtue of the fact that instructions of the first or second computer readable media are stored on the server computer. In addition, a device manufacturer may assemble or provide for assembly all elements of kit embodiments without necessarily offering the elements together to customers.

A kit embodiment may specifically be described to include, a bone alignment device configured to be coupled to a patient, and a first computer readable media containing instructions that are configured to be programmed into a server computer to enable the server computer to transmit information to and receive information from a patient device, and enable the server computer to calculate one or more sets of instructions to be accomplished over predetermined period of time. The kit may also include a second computer readable media containing instructions that are configured to be programmed into the patient device, to enable the patient device to provide information to the patient regarding adjustment of the bone alignment device, and to enable the patient to receive information regarding the state of the bone alignment device. In some embodiments, the prescription is transmitted by the server computer to the patient device and displayed on the patient device, and a revised set of instructions to be accomplished over a predetermined period of time, or in other words, a revised prescription, may be calculated in response at least in part to information received regarding the state of the bone alignment device. The revised prescription may be displayed on the patient device.

In some embodiments, implementing the revised prescription results in alignment of one or more bones of the patient. For example, implementation of the prescription illustrated in FIG. 7 through the fifteenth day listed on FIG. 7 would result in alignment of the fractured tibia and fibula of the patient depicted. Such adjustments may be accomplished by the patient to whom the bone alignment device is coupled or by any person or mechanism cable of carrying out the instructions of the revised prescription.

In some embodiments, the first computer readable media and the second computer readable media are each part of the same physical media.

In some embodiments, the revised prescription is calculated by the server computer and transmitted to the patient computer. In other embodiments, the revised prescription is calculated by the patient device, where the patient device includes further instructions configuring the patient device to calculate one or more sets of instructions to be accomplished over a predetermined period of time.

In some embodiments, the patient device is a patient owned device. The patient device may also be a handheld device.

The first computer readable media may include instructions that are configured to do one or more of the following:

receive a notification that the prescribed adjustment for a particular time period have been completed;

receive information indicating that one or more adjustments have not been made to the bone alignment device in accordance with the set of instructions to be accomplished over a predetermined period of time;

enable the server computer to analyze one or more of the following to calculate the revised set of instructions to be accomplished over a predetermined period of time: pictures of the bone alignment device, information about adjustments of parts of the bone alignment device, information about pain experienced by a patient to whom the bone alignment device is coupled, readings of forces being transmitted through parts of the bone alignment device, and identification information associated with the bone alignment device; and enable the server computer to transmit information to a health care provider, based on information received from the patient device, to schedule a clinical visit for the patient to whom the bone alignment device is coupled.

The second computer readable media may include instructions that are configured to enable the patient device to transmit tracking information from the patient device. For example and without limitation, the patient device may include instructions to push data to the server computer at certain time intervals, when particular compliance factors are met or not met, or when certain functions are activated in the patient device, such as activating the "Done" tag 25 illustrated in FIG. 6. The first computer readable media may include instructions that are configured to enable the server computer to receive tracking information from the patient device and monitor for compliance with the prescription and generate a notice if tracking information is not received from the patient device that confirms compliance with the prescription. The first computer readable media may also include instruction that are configured to enable the server computer to transmit a notice to one or both of the patient device and a device associated with a treating health care provider.

The second computer readable media may include instructions that are configured to enable the patient device to display an image of the bone alignment device at one or more stages of adjustment to illustrate to a patient how the bone alignment device should appear at each stage of adjustment, respectively.

The second computer readable media may include instructions that are configured to enable the patient device to read a unique identifier on the bone alignment device such that when the unique identifier is read by the patient device, the patient device automatically logs into the server computer and transmits information to the server computer. The first computer readable media may include instructions that are configured to enable the server computer to compare the information received from the patient device regarding adjustments made to the bone alignment device to information regarding adjustments scheduled to be performed to carry out the set of instructions to be accomplished over a predetermined period of time. The first computer readable media may include instructions that are configured to enable the server computer to compare the information received from the patient device regarding identity and usage to registered identity and usage information. The first computer readable media may include instructions that are configured to enable the server computer to generate and send notices if the identity and usage information do not match registered identity and usage information.

Figure 8:
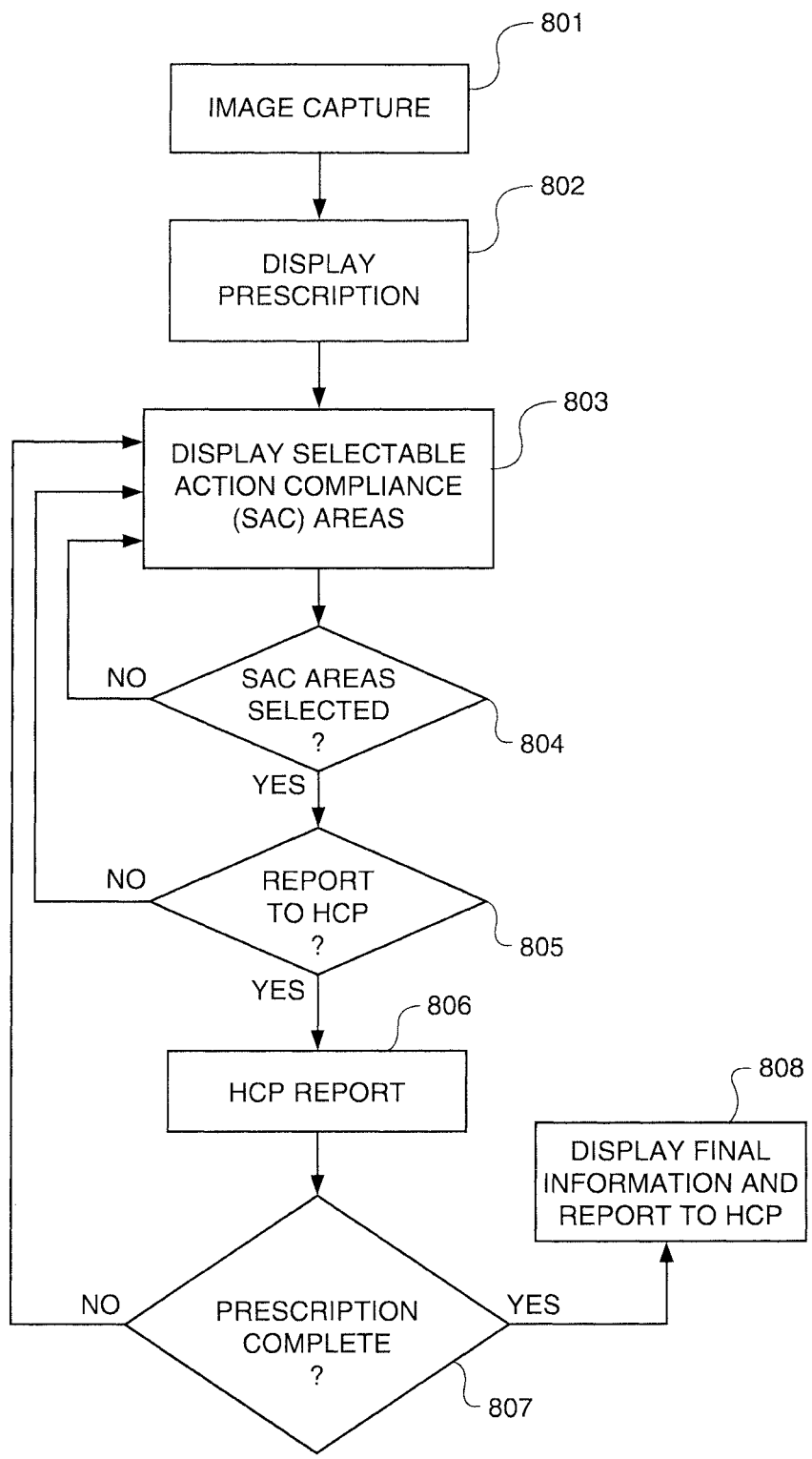
FIG. 8 is a flowchart depicting an embodiment of a method of capturing and processing an image.

A method embodiment is depicted in the flowchart of FIG. 8. In the illustrated embodiment, the method may be accomplished at a multifunction computer with an image capture mechanism. For example, and without limitation, the multifunction computer may be the patient device 2, as described herein and illustrated in FIGS. 1, 5, 6, and 10-15 or a similar device. The image capture mechanism may be an integrated camera, scanner, or similar imaging device, or a separate but compatible imaging device of any effective type. In other embodiments, data may be transferred to the multifunction computer by a technology or method other than imaging. For example, and without limitation, data could be transferred by wireless signal, wired connection, pulsed optical signal, or sound.

Figure 9:
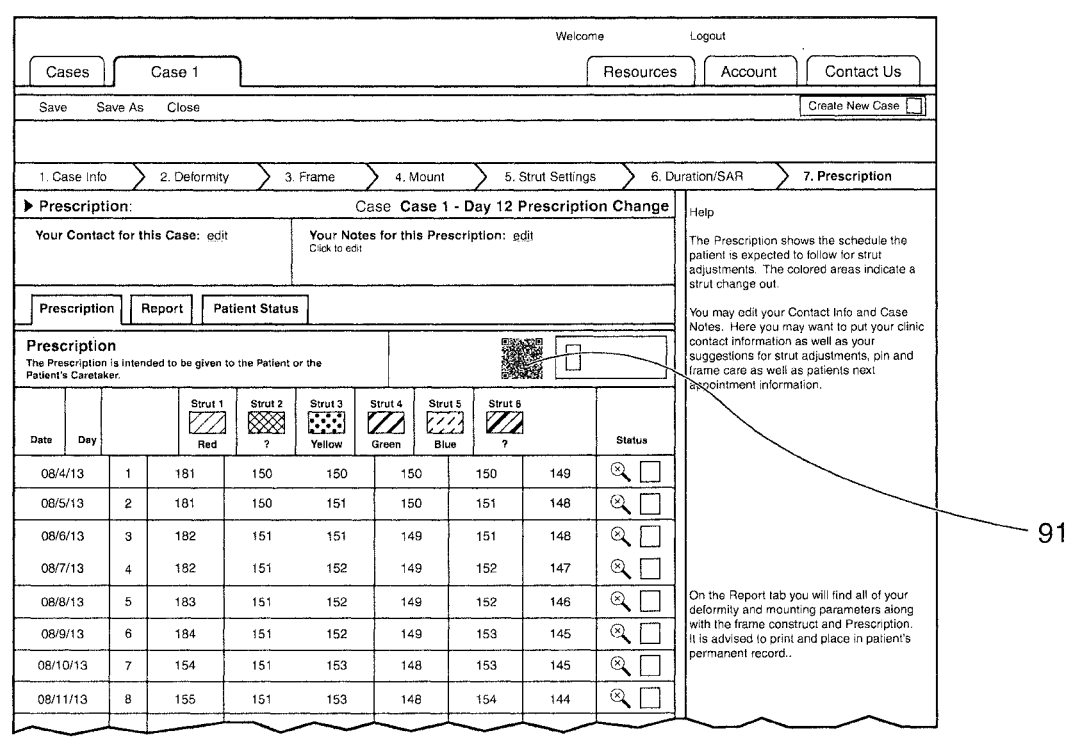

Image capture is represented in FIG. 8 at block 801. An example image capture mechanism may be explained with the aid of FIGS. 9-12. A sample prescription, as may be generated by an HCP, with or without the technical assistance of a device manufacturer, is shown in FIG. 9. The prescription illustrated is generated on an improved version of the website www.spatialframe.com, based on conditions under which a six-axis external fixator is being placed into service. The frame conditions, strut values, and other prescription information for the device shown in FIG. 9 may be encoded into a Quick Response code ("QR") image, such as image 91. Other embodiments may employ any effective type of encoded image. For example, and without limitation, an encoded image may be a conventional barcode, any type of two- or three-dimensional encoded image, or a graphic recognizable by an imaging device that is a pointer or address for a multifunction computer. In this example, the image 91 is provided by an HCP with the aid of software provided by the device manufacturer. Images of various embodiments may be generated by an HCP at greater or lesser degrees of participation by the HCP. The image 91 is shown in FIG. 9 displayed on a computer screen of an HCP device 4 (FIG. 1). However, in other embodiments, an image may be transmitted to a computer or other device at the convenience of a patient. A QR code image or other encoded image in such a case could be transmitted through email, text, social media site, or through any other effective mechanism and displayed on an electronic device for scanning by a patient with the patient device 2 or with any multifunction computer running appropriate software. In other embodiments, a QR code image or other encoded image may be printed on a physical medium and presented or otherwise delivered to a patient for scanning by a patient.

Figure 10:
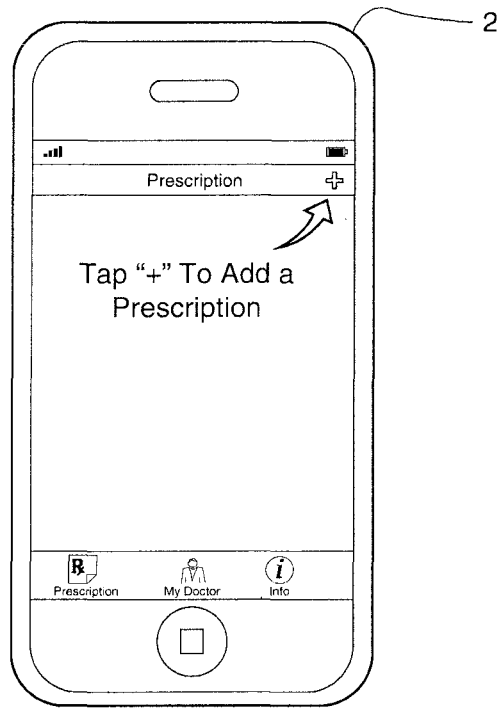
FIG. 10 is a depiction of a patient device displaying a prescription acquisition screen.
Figure 11:
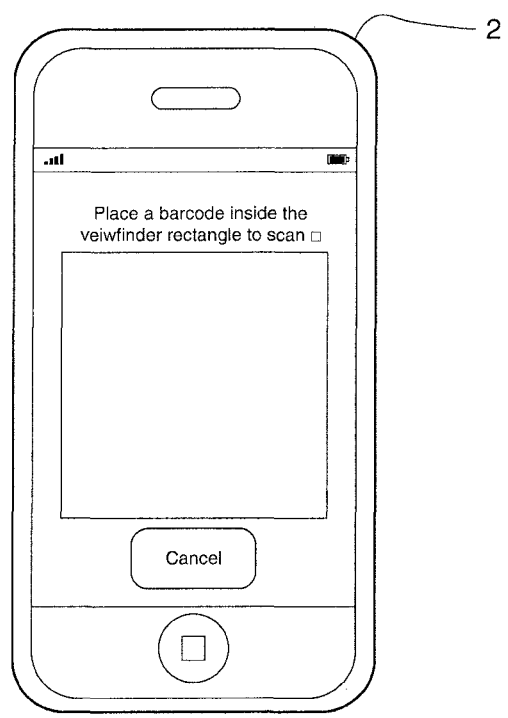
FIG. 11 is a depiction of a patient device displaying a prescription acquisition screen.
Figure 12:
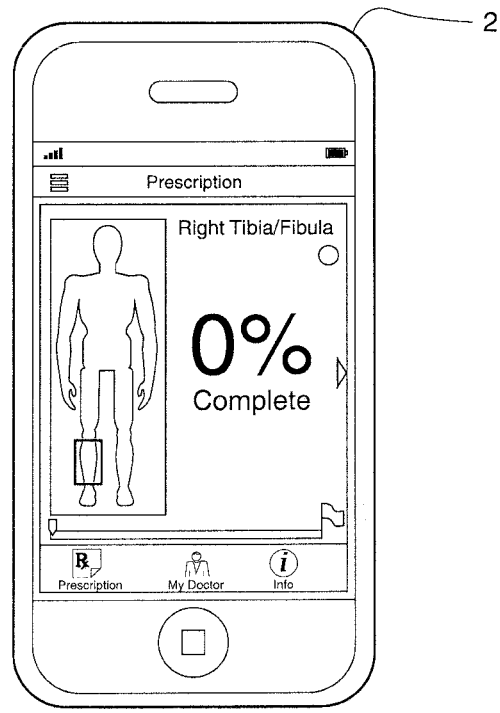
FIG. 12 is a depiction of a patient device displaying a prescription information screen.

The multifunction computer embodied in the patient device 2, as shown in FIGS. 10-12, has an integrated camera. To add a prescription to the multifunction computer, the "+" symbol shown in FIG. 10 is selected. The multifunction computer illustrated in FIG. 10 also shows a form of help text and graphics that is included in some embodiments of the disclosed devices and methods that will be referred to herein as "coach text." Coach text may provide a user with useful information regarding the operation of the multifunction computer. For example, here the coach text graphically shows a user where to tap to add a prescription to the device and explains what will happen as a result of the tapping action.

The result of requesting to add a new prescription to the multifunction computer of the present embodiment is illustrated in FIG. 11. A new screen is opened that instructs a user to "Place a barcode inside the viewfinder rectangle to scan it." The term barcode illustrated refers to a QR code image. In other embodiments, the image may be any effective type that contains information or may direct the multifunction computer to a network or other address where information is located. Continuing with the present example, the multifunction computer embodied in the patient device 2 of FIG. 11 may be used to scan the image 91 shown in FIG. 9 to load all or part of a prescription or address information that correlates with a prescription into the multifunction computer, as illustrated in FIG. 12, and as represented in block 802 of FIG. 8. A summary and a progress indicator of the prescription are depicted in FIG. 12 loaded into the patient device 2, thereby displaying at least a portion of the prescription on the multifunction computer. In the illustrated embodiment, scanning of the image 91 enables the patient device 2 to contact the server computer 3 (FIG. 1) through the network 5, and the server computer 3 provides prescription details, including all daily adjustments and surgeon contact information to the patient device 2. Either direct prescription information or address information directing the patient device 2 to further prescription information are considered data specifying at least a portion of a prescription as used herein.

Figure 13:
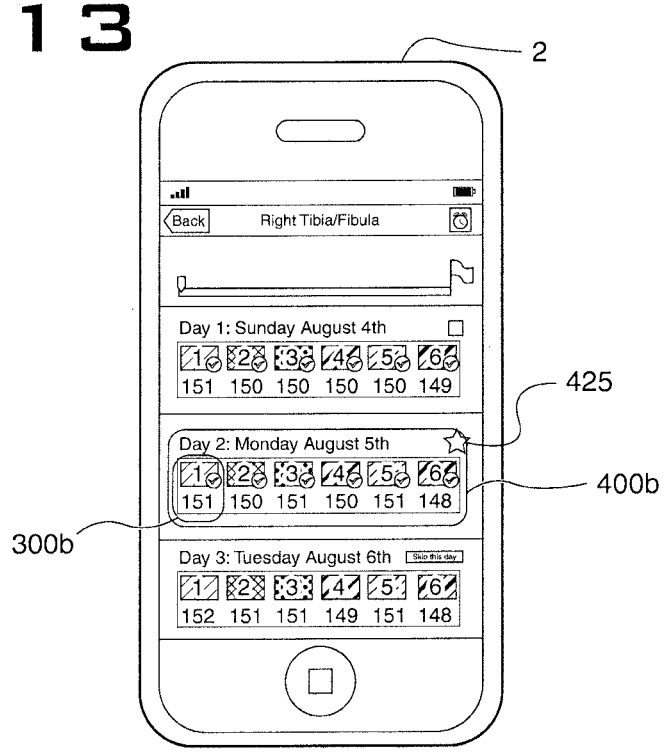
FIG. 13 is a depiction of a patient device displaying multiple days of a prescription for a bone alignment device.
Figure 15:
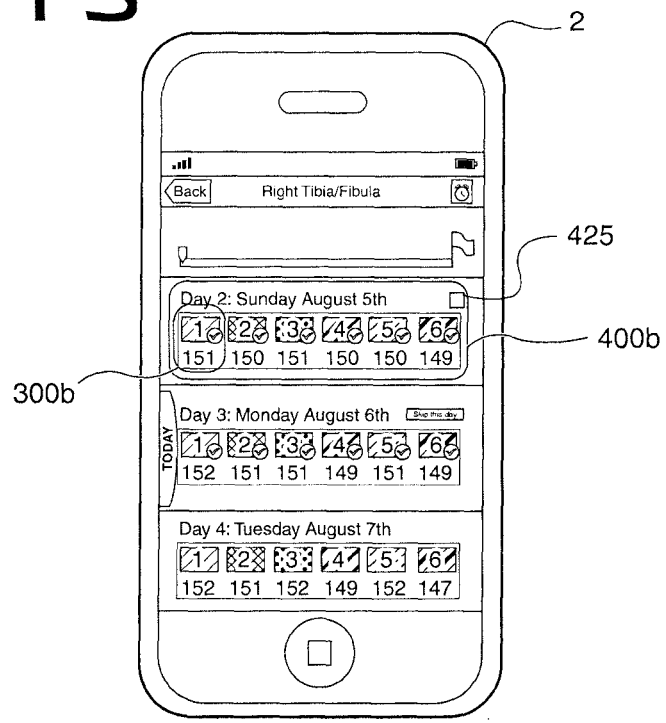
FIG. 15 is a depiction of a patient device displaying multiple days of a prescription for a bone alignment device.

Selectable action compliance areas 300a and 300b are illustrated in FIGS. 5, 6, 13 and 15. Each embodiment includes additional selectable action compliance areas that correlate with each element of the medical device 1 to form a set 400a (FIG. 6), 400b (FIGS. 13 and 15). Set 400a, 400b groups together all of the selectable action compliance areas for a day of an associated prescription. Each of the display areas includes a color that correlates with a color present on an adjustable element of the medical device 1 (FIG. 1), a value to which an adjustable element of the medical device 1 should be adjusted, and an indicium of completion that is activated when a user inputs into the computer that the value to which an adjustable element of the medical device 1 should be adjusted in accordance with the prescription has been adjusted. Values illustrated in the example embodiments are 179 mm in selectable action compliance area 300a (FIGS. 5-6) and 151 mm in selectable action compliance area 300b (FIGS. 13 and 15). Example indicia of completion in selectable action compliance areas 300a, 300b of the illustrated embodiments are a checkmark and color change in FIG. 5, an encircled checkmark in FIG. 6, an encircled checkmark in FIG. 13, and an encircled checkmark in FIG. 15. Indicia of completion in various embodiments may be any one or more of a change in text, a change in font, a change in color, an added character or symbol, and any other effective designator, sound, or activation.

In the embodiments illustrated in FIGS. 5, 6, 13 and 15, the selectable action compliance areas 300a, 300b are displayed on a touch screen. Each selectable action compliance area correlates with an element of a medical device. In this example, six selectable action compliance areas in each of the embodiments correlate with one each of the six elements of the medical device 1. When each element of the medical device 1 is adjusted in accordance with at least a portion of the prescription, the selectable action compliance area in these examples is configured to be touched and thereby selected. Specifically, when the box next to the 179 mm value in the selectable action compliance area 300a was touched, following adjustment of Strut 1 in compliance with the Day 12 requirement of the prescription, the selectable action compliance area 300a was selected. When the selectable action compliance area 300b was touched, following adjustment of Strut 1 to 151 mm in compliance with the Day 2 requirement of the prescription, the selectable action compliance area 300b was selected. In other embodiments, selectable action compliance areas may be selectable with any type of effective pointing device. For example, and without limitation, pointing devices may include a touchpad, a mouse, a rollerball, a digitizing pad, and a light emitting pointing device.

As listed in FIG. 8, block 803, method embodiments may include displaying selectable action compliance areas on a screen of the multifunction computer that are to be selected when one or more portions of the prescription are completed. Method embodiments may also include selection of selectable action compliance areas, as depicted in block 804 of FIG. 8. Until selection of a selectable action compliance area is detected, the method will continue to display the selectable action compliance areas. When a selectable action compliance area is selected, "Yes" at block 804, the illustrated method will check whether to report the selection to the HCP (block 805). If no report is to be made, the method will return and continue to display selectable action compliance areas. If a report to an HCP is to be made (block 806), a report will be made according to the criteria set in the associated program. Reporting to the HCP may be automatically initiated by the multifunction computer in some embodiments, or may require operator intervention in some embodiments. Automatic reporting events may include selection of one or more of the selectable action compliance areas. For example, when each selectable action compliance area, such as selectable action compliance areas 300a, 300b is selected, the multifunction computer may report the event to the HCP. In other embodiments, the multifunction computer may report to the HCP only after a predetermined number or set of selectable action compliance areas are selected. For example, and without limitation, the multifunction computer may report to the HCP after a one-day group of selectable action compliance areas, such as set 400a or set 400b (FIGS. 6, 13 and 14), have been selected. Triggers for reporting to an HCP may be configurable at one or more of the patient device 2, the server computer 3, and the HCP device 4 (FIG. 1).

After a report to an HCP has been made, block 806 of FIG. 8, the illustrated method checks to see if the prescription selected is complete (block 807). If the prescription is not complete, the method will return and continue to display selectable action compliance areas. If the prescription is complete, the method is configured to display final prescription information and report a completed prescription to the HCP (block 808).

An embodiment of the invention is a graphical user interface on the multifunction computer with an image capture mechanism. For example, the patient device 2 is a multifunction computer, as shown in FIG. 11. The multifunction computer includes an image capture mechanism when a selectable image capture area is designated, and the multifunction computer captures an image including data that specifies at least a portion of a prescription provided by an HCP, as discussed herein in association with FIGS. 9-12. The graphical user interface on the multifunction computer displays at least a portion of the prescription on the multifunction computer, and displays one or more of the selectable action compliance areas 300*a*, 300*b*, and others, on the multifunction computer that are to be selected when one or more portions of the prescription or completed.

In the embodiments illustrated in FIGS. 5, 6, 13 and 15, the selectable action compliance areas 300*a*, 300*b* are displayed on a touch screen graphical user interface. Each selectable action compliance area correlates with an element of a medical device. In this example, six selectable action compliance areas in each of the embodiments correlate with one each of the six elements of the medical device 1. When each element of the medical device 1 is adjusted in accordance with at least a portion of the prescription, the selectable action compliance area in these examples is configured to be touched and thereby selected. Specifically, when the box next to the 179 mm value in the selectable action compliance area 300*a* was touched, following adjustment of Strut 1 in compliance with the Day 12 requirement of the prescription, the selectable action compliance area 300*a* was selected. When the selectable action compliance area 300*b* was touched, following adjustment of Strut 1 to 151 mm in compliance with the Day 2 requirement of the prescription, the selectable action compliance area 300*b* was selected. In other embodiments, selectable action compliance areas may be selectable with any type of effective pointing device. For example, and without limitation, pointing devices may include a touchpad, a mouse, a rollerball, a digitizing pad, and a light emitting pointing device.

In some embodiments, in response to detecting selection of one or more of the selectable action compliance areas, the multifunction computer reports selection of the selectable action compliance areas to the HCP. More particularly in the illustrated embodiments, when a selectable action compliance area is selected, programming supporting the graphical user interface will check whether to report the selection to the HCP. If no report is to be made, the graphical user interface will continue to display selectable action compliance areas. If a report to an HCP is to be made, a report will be made according to the criteria set in the associated program. Reporting to the HCP may be automatically initiated by the multifunction computer in some embodiments, or may require operator intervention in some embodiments. Automatic reporting events may include selection of one or more of the selectable action compliance areas on the graphical user interface. For example, when each selectable action compliance area, such as selectable action compliance areas 300*a*, 300*b* is selected, the multifunction computer may report the event to the HCP. In other embodiments, the multifunction computer may report to the HCP only after a predetermined number or set of selectable action compliance areas are selected. For example, and without limitation, the multifunction computer may report to the HCP after a one-day group of selectable action compliance areas, such as set 400*a* or set 400*b* (FIGS. 6, 13 and 14), have been selected. Triggers for reporting to an HCP may be configurable at one or more of the patient device 2, the server computer 3, and the HCP device 4 (FIG. 1).

Another embodiment of the invention is a non-transitory computer readable storage medium storing one or more programs, the one or more programs comprising instructions, which when executed by a multifunction computer with an image capture mechanism, cause the computer to be configured to capture an image provided by an HCP. For example, the patient device 2 is a multifunction computer, as shown in FIG. 11. The multifunction computer includes an image capture mechanism when a selectable image capture area is designated, and the multifunction computer captures an image including data that specifies at least a portion of a prescription provided by an HCP, as discussed herein in association with FIGS. 9-12.

In response to the data specifying at least a portion of a prescription, the instructions may further cause the multifunction computer to display at least a portion of the prescription on the multifunction computer. For example, in the embodiments illustrated in FIGS. 5, 6, 13, and 15, the selectable action compliance areas 300*a*, 300*b* are displayed on a touch screen of the multifunction computer. Each selectable action compliance area correlates with an element of a medical device. In this example, six selectable action compliance areas in each of the embodiments correlate with one each of the six elements of the medical device 1. When each element of the medical device 1 is adjusted in accordance with at least a portion of the prescription, the selectable action compliance area in these examples is configured to be touched and thereby selected. Specifically, when the box next to the 179 mm value in the selectable action compliance area 300*a* was touched, following adjustment of Strut 1 in compliance with the Day 12 requirement of the prescription, the selectable action compliance area 300*a* was selected. When the selectable action compliance area 300*b* was touched, following adjustment of Strut 1 to 151 mm in compliance with the Day 2 requirement of the prescription, the selectable action compliance area 300*b* was selected. In other embodiments, selectable action compliance areas may be selectable with any type of effective pointing device. For example, and without limitation, pointing devices may include a touchpad, a mouse, a rollerball, a digitizing pad, and a light emitting pointing device.

In some embodiments, instructions are provided such that in response to detecting selection of one or more of the selectable action compliance areas, the multifunction computer reports selection of the selectable action compliance areas to the HCP. More particularly in the illustrated embodiments, when a selectable action compliance area is selected, instructions will check whether to report the selection to the HCP. If no report is to be made, the multifunction computer will continue to display selectable action compliance areas. If a report to an HCP is to be made, a report will be made according to the criteria set in the associated program. Reporting to the HCP may be automatically initiated by the multifunction computer in some embodiments, or may require operator intervention in some embodiments. Automatic reporting events may include selection of one or more of the selectable action compliance areas. For example, when each selectable action compliance area, such as selectable action compliance areas 300a, 300b is selected, the multifunction computer may report the event to the HCP. In other embodiments, the multifunction computer may report to the HCP only after a predetermined number or set of selectable action compliance areas are selected. For example, and without limitation, the multifunction computer may report to the HCP after a one-day group of selectable action compliance areas, such as set 400a or set 400b (FIGS. 6, 13 and 14), have been selected. Triggers for reporting to an HCP may be configurable at one or more of the patient device 2, the server computer 3, and the HCP device 4 (FIG. 1).

Figure 16:
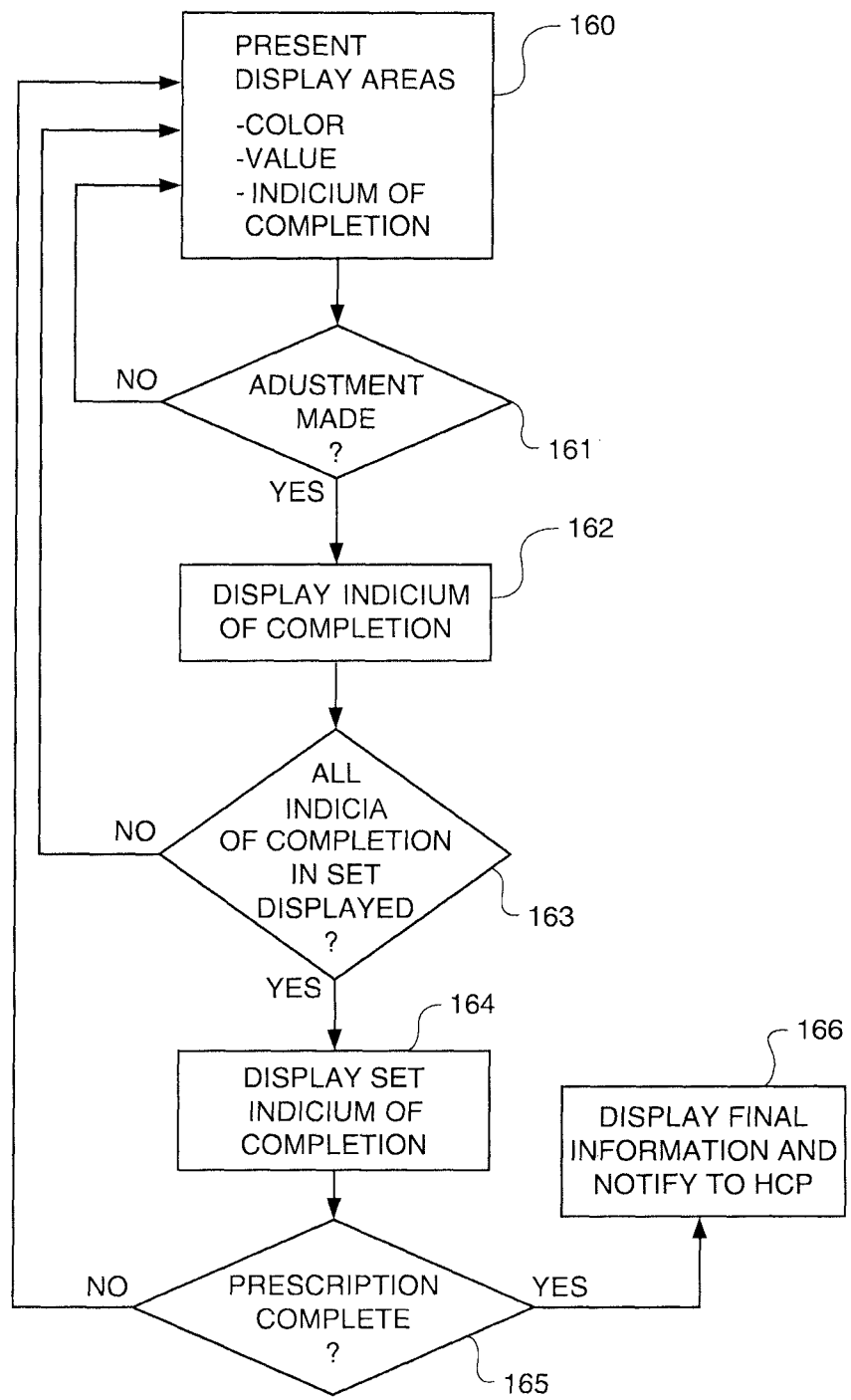
FIG. 16 is a flowchart depicting an embodiment of a method of displaying values associated with adjustment of a medical device and graphically representing compliance with a prescription.

Another embodiment of the invention is a computer implemented method of displaying values associated with adjustments of medical device elements for which a prescription for adjusting the medical device has been provided, and of graphically representing compliance of the adjustments with the prescription. A flowchart representative of the method is illustrated in FIG. 16. As shown in block 160 of FIG. 16, the method includes presenting two or more display areas in a set, each display area correlating with at least one adjustable element of a medical device. Example display areas are illustrated in the selectable action compliance areas 300a and 300b of FIGS. 5, 6, 13 and 15. Each embodiment includes additional selectable action compliance areas that correlate with each element of the medical device 1 to form a set 400a (FIG. 6), 400b (FIGS. 13 and 15) of six display areas. Set 400a, 400b groups together all of the selectable action compliance areas for a day of an associated prescription. Other embodiments may include sets grouped together by another period of time. Each of the display areas includes a color that correlates with a color present on an adjustable element of the medical device 1 (FIG. 1), a value to which an adjustable element of the medical device 1 should be adjusted, and an indicium of completion that is activated when a user inputs into the computer that the value to which an adjustable element of the medical device 1 should be adjusted in accordance with the prescription has been adjusted. Values illustrated in the example embodiments are 179 mm in selectable action compliance area 300a (FIGS. 5 and 6) and 151 mm in selectable action compliance area 300b (FIGS. 13 and 15). Example indicia of completion in selectable action compliance areas 300a, 300b of the illustrated embodiments are a checkmark and color change in FIG. 5, an encircled checkmark in FIG. 6, an encircled checkmark in FIG. 13, and an encircled checkmark in FIG. 15. Indicium of completion in various embodiments may be any one or more of a change in text, a change in font, a change in color, an added character or symbol, and any other effective designator, sound, or activation.

In the method illustrated in FIG. 16, the computing device at block 161 checks whether or not an adjustment has been made to a display area. If no adjustment has been made, the method continues to present display areas (block 160). If an adjustment has been made in an indicium of completion regarding the display area then an indicium of completion is displayed, as illustrated in block 162. Embodiments of the method may then include a check to determine whether all indicia of completion in a set, as defined in associated prescription, have been displayed (block 163). If all indicia of completion in a set have not been displayed, the method continues to present display areas (block 160). If all indicia of completion in a set have been displayed, then the computer may display a set indicium of completion, as described in block 164. Example set indicia of completion in the illustrated embodiments include the "Done" tag 25 (FIG. 6) and the star symbol 425 (FIGS. 13 and 15). Set indicia of completion in various embodiments may be any one or more of a change in text, a change in font, a change in color, an added character or symbol, and any other effective designator, sound, or activation. Embodiments of the method may then check to see if the prescription is complete (block 165). If the prescription is not complete, then the method continues to present display areas (block 160). If the prescription is complete then embodiments of the method will display final information regarding the prescription and compliance with the prescription and may notify the HCP (block 166).

Figure 14:
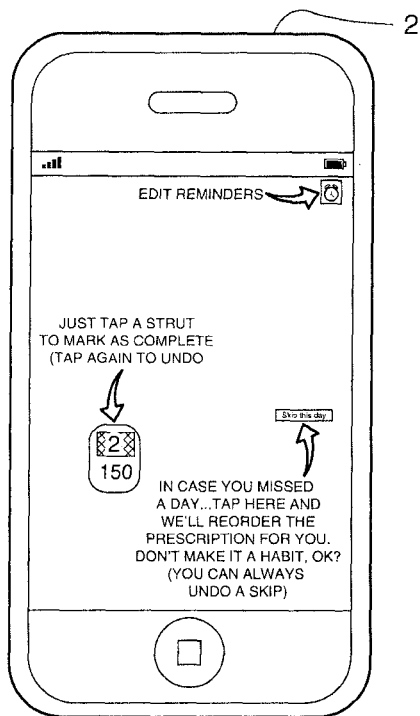
FIG. 14 is a depiction of a patient device displaying multiple days of a prescription for a bone alignment device and associated coach text.

Notification of the HCP may occur at one or more stages of the prescription and may be a direct or indirect notification. Notification may go specifically from the patient device 2, through the network 5, and to the HCP device 4 (FIG. 1), or may be through any other effective mode of communication, such as but not limited to, email, text, fax, social media, and letter. Notification may also be one or more facilitated by the server computer 3 (FIG. 1), a device manufacturer, a computer system or network manufacturer, and any other service provider. If a notification of an HCP is to be made, notice will be made according to the criteria set in an associated program. Notification of the HCP may be automatically initiated by the multifunction computer in some embodiments, or may require operator intervention in some embodiments. Automatic reporting events may include activation of one or more of the indicia of completion. For example, when each display area, such as selectable action compliance areas 300a, 300b is selected, the multifunction computer may notify the HCP. In other embodiments, the multifunction computer may notify the HCP only after a predetermined number or set of indicia of completion have been activated. For example, and without limitation, the multifunction computer may notify the HCP after a one-day group of indicia of completion (i.e., a set indicium of completion, such as set 400a or set 400b; FIGS. 6, 13 and 14) have been activated. Triggers for notifying an HCP may be configurable at one or more of the patient device 2, the server computer 3, and the HCP device 4 (FIG. 1).

Another embodiment of the invention is a graphical user interface for a multifunction computer with a display, the graphical user interface may include two or more display areas in a set, each display area correlating with at least one adjustable element of a medical device. Example display areas are illustrated in the selectable action compliance areas 300a and 300b of FIGS. 5, 6, 13 and 15. Each embodiment includes additional selectable action compliance areas that correlate with each element of the medical device 1 to form a set 400a (FIG. 6), 400b (FIGS. 13 and 15) of six display areas. Set 400a, 400b groups together all of the selectable action compliance areas for a day of an associated prescription. Other embodiments may include sets grouped together by another period of time. Each of the display areas includes a color that correlates with a color present on an adjustable element of the medical device 1 (FIG. 1), a value to which an adjustable element of the medical device 1 should be adjusted, and an indicium of completion that is activated when a user inputs into the computer that the value to which an adjustable element of the medical device 1 should be adjusted in accordance with the prescription has been adjusted. Values illustrated in the example embodiments are 179 mm in selectable action compliance area 300a (FIGS. 5 and 6) and 151 mm in selectable action compliance area 300b (FIGS. 13 and 15). Example indicia of completion in selectable action compliance areas 300a, 300b of the illustrated embodiments are a checkmark and color change in FIG. 5, an encircled checkmark in FIG. 6, an encircled checkmark in FIG. 13, and an encircled checkmark in FIG.

15. Indicium of completion in various embodiments may be any one or more of a change in text, a change in font, a change in color, an added character or symbol, and any other effective designator, sound, or activation.

The graphical user interface may also include a set indicium of completion that is activated when all indicia of completion associated with two or more display areas in a set have been activated. When all indicia of completion in a set have been displayed, then the computer may display a set indicium of completion. Example set indicia of completion in the illustrated embodiments include the "Done" tag 25 (FIG. 6) and the star symbol 425 (FIGS. 13 and 15). Set indicia of completion in various embodiments may be any one or more of a change in text, a change in font, a change in color, an added character or symbol, and any other effective designator, sound, or activation.

Another embodiment of the invention is a computer program product comprising a non-transitory computer readable medium encoded with program instruction that, when executed by a processor in a multifunction computer, cause the processor to execute a method that may include presenting two or more display areas in a set, each display area correlating with at least one adjustable element of a medical device. Example display areas are illustrated in the selectable action compliance areas 300*a* and 300*b* of FIGS. 5, 6, 13 and 15. Each embodiment includes additional selectable action compliance areas that correlate with each element of the medical device 1 to form a set 400*a* (FIG. 6), 400*b* (FIGS. 13 and 15) of six display areas. Set 400*a*, 400*b* groups together all of the selectable action compliance areas for a day of an associated prescription. Other embodiments may include sets grouped together by another period of time. Each of the display areas includes a color that correlates with a color present on an adjustable element of the medical device 1 (FIG. 1), a value to which an adjustable element of the medical device 1 should be adjusted, and an indicium of completion that is activated when a user inputs into the computer that the value to which an adjustable element of the medical device 1 should be adjusted in accordance with the prescription has been adjusted. Values illustrated in the example embodiments are 179 mm in selectable action compliance area 300*a* (FIGS. 5 and 6) and 151 mm in selectable action compliance area 300*b* (FIGS. 13 and 15). Example indicia of completion in selectable action compliance areas 300*a*, 300*b* of the illustrated embodiments are a checkmark and color change in FIG. 5, an encircled checkmark in FIG. 6, an encircled checkmark in FIG. 13, and an encircled checkmark in FIG. 15. Indicium of completion in various embodiments may be any one or more of a change in text, a change in font, a change in color, an added character or symbol, and any other effective designator, sound, or activation.

Indicium of completion for the two or more display areas are displayed when a user inputs into the computer that the value to which an adjustable element of the medical device should be adjusted in accordance with the prescription has been adjusted. If all indicia of completion in a set have been displayed, then the computer under the present method embodiment displays a set indicium of completion. Example set indicia of completion in the illustrated embodiments include the "Done" tag 25 (FIG. 6) and the star symbol 425 (FIGS. 13 and 15). Set indicia of completion in various embodiments may be any one or more of a change in text, a change in font, a change in color, an added character or symbol, and any other effective designator, sound, or activation.

Notification of the HCP may occur at one or more stages of the prescription and may be a direct or indirect notification. Notification may go specifically from the patient device 2, through the network 5, and to the HCP device 4 (FIG. 1), or may be through any other effective mode of communication, such as but not limited to, email, text, fax, social media, and letter. Notification may also be one or more facilitated by the server computer 3 (FIG. 1), a device manufacturer, a computer system or network manufacturer, and any other service provider. If a notification of an HCP is to be made, notice will be made according to the criteria set in an associated program. Notification of the HCP may be automatically initiated by the multifunction computer in some embodiments, or may require operator intervention in some embodiments. Automatic reporting events may include activation of one or more of the indicia of completion. For example, when each display area, such as selectable action compliance areas 300*a*, 300*b* is selected, the multifunction computer may notify the HCP. In other embodiments, the multifunction computer may notify the HCP only after a predetermined number or set of indicia of completion have been activated. For example, and without limitation, the multifunction computer may notify the HCP after a one-day group of indicia of completion (i.e., a set indicium of completion, such as set 400*a* or set 400*b*; FIGS. 6, 13 and 14) have been activated. Triggers for notifying an HCP may be configurable at one or more of the patient device 2, the server computer 3, and the HCP device 4 (FIG. 1).

Similar to the coach text illustrated and described in association with FIG. 10 herein, additional coach text is shown in FIG. 14. Coach text may provide a user with useful information regarding the operation of the multifunction computer. For example, here the coach text graphically shows a user where to activate the screen of the patient device 2 to accomplish tasks that are currently available on the screen of the patient device 2. For example, coach text is included in FIG. 14 that instructs a user how to mark a strut adjustment as complete and how to undo a designation as complete. Coach text is also provided to instruct a patient in case the patient missed a day of adjustments. In addition, the coach text encourages the patient not to make a habit of noncompliance. The noted "skip this day" button provides a shortcut for a patient to initiate a New Total Residual within predefined limits. The final coach text illustrated in FIG. 14 directs a user to a button that allows the user to edit reminders associated with a prescription. In some embodiments, coach text may appear automatically when the patient device 2 is awaiting user input. In other embodiments, coach text may need to be requested by a user, or may appear when a user is apparently having difficulty navigating an application.

One form of the invention is directed to a graphical user interface on a multifunction computer with an image capture mechanism, the graphical user interface comprising: a selectable image capture area; and selectable action compliance areas that correlate with an elements of a medical device; wherein: in response to detecting designation of the selectable image capture area, the multifunction computer captures an image including data that specifies at least a portion of a prescription provided by a health care provider, displays at least a portion of the prescription on the multifunction computer, and displays one or more of the selectable action compliance areas on the multifunction computer that are to be selected when one or more portions of the prescription are completed; and in response to detecting selection of one or more of the selectable action compliance areas, the multifunction computer reports selection of the selectable action compliance areas to the health care provider.

In one aspect of the invention, the multifunction computer captures an image generated in response to a prescription for treatment calculated by the health care provider, and wherein the image has been displayed on an electronic device.

In another aspect of the invention, the multifunction computer captures an image generated in response to a prescription for treatment calculated by the health care provider, and wherein the image has been applied to a physical medium.

In another aspect of the invention, the multifunction computer captures an image of a Quick Response code.

In another aspect of the invention, the multifunction computer includes a selectable area on a touch screen, wherein the selectable action compliance area correlates with an element of a medical device, and wherein when the element of the medical device is adjusted in accordance with at least a portion of the prescription, the selectable action compliance area is configured to be touched and thereby selected.

In another aspect of the invention, the multifunction computer automatically initiates contact with the health care provider when each selectable action compliance area is selected.

In another aspect of the invention, the multifunction computer automatically initiates contact with the health care provider when a predetermined number or set of selectable action compliance areas are selected.

Another form of the invention is directed to a non-transitory computer readable storage medium storing one or more programs that comprise instruction, which when executed by a multifunction computer with an image capture mechanism, cause the computer to: be configured to capture an image provided by a health care provider, wherein the image includes data specifying at least a portion of a prescription; and in response to the data specifying at least a portion of a prescription: display at least a portion of the prescription on the multifunction computer; display selectable action compliance areas on a screen of the multifunction computer that are to be selected when one or more portions of the prescription are completed; and report selection of the selectable action compliance areas to the health care provider when the selectable action compliance areas are selected on the multifunction computer.

In one aspect of the invention, the image provided by a health care provider is an image generated in response to a prescription for treatment calculated by the health care provider, and wherein the image has been displayed on an electronic device.

In another aspect of the invention, the image provided by a health care provider is an image generated in response to a prescription for treatment calculated by the health care provider, and wherein the image has been applied to a physical medium.

In another aspect of the invention, the image provided by a health care provider is an image of a Quick Response code.

In another aspect of the invention, reporting selection of the selectable action compliance areas is automatically initiated by the multifunction computer when each selectable action compliance area is selected.

In another aspect of the invention, reporting selection of the selectable action compliance areas is automatically initiated by the multifunction computer when a predetermined number or set of selectable action compliance areas are selected.

Another form of the invention is directed to a computer implemented method of displaying values associated with adjustments of medical device elements for which a prescription for adjusting the medical device has been provided, and of graphically representing compliance of the adjustments with the prescription, comprising: presenting two or more display areas in a set, each display area correlating with at least one adjustable element of a medical device, and each display area including: a color that correlates with a color present on an adjustable element of the medical device, a value to which an adjustable element of the medical device should be adjusted, and an indicium of completion that is activated when a user inputs into the computer that the value to which an adjustable element of the medical device should be adjusted in accordance with the prescription has been adjusted; displaying the indicia of completion for the two or more display areas; and displaying a set indicium of completion when all indicia of completion associated with two or more display areas in a set have been activated.

In one aspect of the invention, the act of presenting two or more display areas in a set includes presenting six display areas in a set.

In another aspect of the invention, the act of presenting two or more display areas in a set includes displaying a set associated with prescribed adjustments for a particular period of time.

In another aspect of the invention, the particular period of time is a day.

In another aspect of the invention, the indicium of completion is a check mark placed within an associated display area.

In another aspect of the invention, the indicium of completion is one or more of a change in text, a change in font, a change in color, and an added character or symbol.

In another aspect of the invention, the method further comprises notifying a health care provider when a user inputs into the computer that the value to which an adjustable element of the medical device should be adjusted has been adjusted.

In another aspect of the invention, the method further comprises notifying a health care provider when a user inputs into the computer that a set of values to which a set of adjustable elements of the medical device should be adjusted have been adjusted.

Another form of the invention is directed to a graphical user interface for a multifunction computer with a display, the graphical user interface comprising: two or more display areas in a set, each display area correlating with at least one adjustable element of a medical device, and each display area including: a color that correlates with a color present on an adjustable element of the medical device, a value to which an adjustable element of the medical device should be adjusted, and an indicium of completion that is activated when a user inputs into the computer that the value to which an adjustable element of the medical device should be adjusted in accordance with the prescription has been adjusted; and a set indicium of completion that is activated when all indicia of completion associated with two or more display areas in a set have been activated.

In one aspect of the invention, the two or more display areas in a set include six display areas in a set.

In another aspect of the invention, each set of display areas is associated with prescribed adjustments for a particular period of time.

In another aspect of the invention, the particular period of time is a day.

In another aspect of the invention, the indicium of completion is a check mark placed within an associated display area.

In another aspect of the invention, the indicium of completion is one or more of a change in text, a change in font, a change in color, and an added character or symbol.

Another form of the invention is directed to a computer program product comprising a non-transitory computer readable medium encoded with program instruction that, when executed by a processor in a multifunction computer, cause the processor to execute a method comprising: presenting two or more display areas in a set, each display area correlating with at least one adjustable element of a medical device, and each display area including: a color that correlates with a color present on an adjustable element of the medical device, a value to which an adjustable element of the medical device should be adjusted, and an indicium of completion that is activated when a user inputs into the computer that the value to which an adjustable element of the medical device should be adjusted in accordance with the prescription has been adjusted; displaying indicia of completion for the two or more display areas; and displaying a set indicium of completion when all indicia of completion associated with two or more display areas in a set have been activated.

In one aspect of the invention, the act of presenting two or more display areas in a set includes presenting six display areas in a set.

In another aspect of the invention, the act of presenting two or more display areas in a set includes displaying a set associated with prescribed adjustments for a particular period of time.

In another aspect of the invention, the particular period of time is a day.

In another aspect of the invention, the indicium of completion is a check mark placed within an associated display area.

In another aspect of the invention, the indicium of completion is one or more of a change in text, a change in font, a change in color, and an added character or symbol.

In another aspect of the invention, the method further comprises notifying a health care provider when a user inputs into the computer that the value to which an adjustable element of the medical device should be adjusted has been adjusted.

In another aspect of the invention, the method further comprises notifying a health care provider when a user inputs into the computer that a set of values to which a set of adjustable elements of the medical device should be adjusted have been adjusted.

Another form of the invention is directed to a kit for use in treating a patient in accordance with a set of instructions to be accomplished over a predetermined period of time, comprising: a bone alignment device configured to be coupled to a patient; a first computer readable media containing instructions that are configured to: be programmed into a server computer, enable the server computer to transmit information to and receive information from a patient device, and enable the server computer to calculate one or more sets of instructions to be accomplished over a predetermined period of time; and a second computer readable media containing instructions that are configured to: be programmed into the patient device, enable the patient device to provide information to the patient regarding adjustment of the bone alignment device, and enable the patient device to receive information regarding the state of the bone alignment device; wherein the set of instructions to be accomplished over a predetermined period of time is transmitted by the server computer to the patient device and displayed on the patient device; wherein a revised set of instructions to be accomplished over a predetermined period of time is calculated in response at least in part to information received regarding the state of the bone alignment device; and wherein the revised set of instructions to be accomplished over a predetermined period of time is displayed on the patient device.

In one aspect of the invention, implementing the revised set of instructions by adjustment of the bone alignment device results in alignment of one or more bones of the patient.

In another aspect of the invention, adjustment of the bone alignment device is accomplished by the patient to whom the bone alignment device is coupled.

In another aspect of the invention, the first computer readable media and the second computer readable media are each part of the same physical media.

In another aspect of the invention, the revised set of instructions is calculated by the server computer and transmitted to the patient device.

In another aspect of the invention, the revised set of instructions is calculated by the patient device, and wherein the patient device includes further instructions configuring the patient device to calculate one or more sets of instructions to be accomplished over a predetermined period of time.

In another aspect of the invention, the patient device is a patient owned device.

In another aspect of the invention, the patient device is a patient owned handheld device.

In another aspect of the invention, the first computer readable media includes instructions that are configured to receive a notification that the prescribed adjustments for a particular time period have been completed.

In another aspect of the invention, the first computer readable media includes instructions that are configured to receive information indicating that one or more adjustments have not been made to the bone alignment device in accordance with the set of instructions to be accomplished over a predetermined period of time.

In another aspect of the invention, the second computer readable media includes instructions that are configured to enable the patient device to transmit tracking information from the patient device.

In another aspect of the invention, the first computer readable media includes instructions that are configured to enable the server computer to receive tracking information from the patient device and monitor for compliance with the set of instructions to be accomplished and generate a notice if tracking information is not received from the patient device that confirms compliance with the set of instructions.

In another aspect of the invention, the first computer readable media includes instructions that are configured to enable the server computer to transmit a notice to the patient device.

In another aspect of the invention, the first computer readable media includes instructions that are configured to enable the server computer to transmit a notice to a device associated with a treating health care provider.

In another aspect of the invention, the first computer readable media includes instructions that are configured to enable the server computer to analyze one or more of the following to calculate the revised set of instructions to be accomplished over a predetermined period of time: pictures of the bone alignment device, information about adjustments of parts of the bone alignment device, information about pain experienced by a patient to whom the bone alignment device is coupled, readings of forces being transmitted through parts of the bone alignment device, and identification information associated with the bone alignment device.

In another aspect of the invention, the second computer readable media includes instructions that are configured to enable the patient device to display an image of the bone alignment device at one or more stages of adjustment to illustrate to a patient how the bone alignment device should appear at each stage of adjustment, respectively.

In another aspect of the invention, the second computer readable media includes instructions that are configured to enable the patient device to read a unique identifier on the bone alignment device such that when the unique identifier is read by the patient device, the patient device automatically logs into the server computer and transmits information to the server computer.

In another aspect of the invention, the first computer readable media includes instructions that are configured to enable the server computer to compare the information received from the patient device regarding adjustments made to the bone alignment device to information regarding adjustments scheduled to be performed to carry out the set of instructions to be accomplished over a predetermined period of time.

In another aspect of the invention, the first computer readable media includes instructions that are configured to enable the server computer to compare the information received from the patient device regarding identity and usage to registered identity and usage information.

In another aspect of the invention, the first computer readable media includes instructions that are configured to enable the server computer to generate and send notices if the identity and usage information do not match registered identity and usage information.

In another aspect of the invention, the first computer readable media includes instructions that are configured to enable the server computer to transmit information to a health care provider, based on information received from the patient device, to schedule a clinical visit for the patient to whom the bone alignment device is coupled.

Another form of the invention is directed to a method of changing a prescription for a bone alignment device coupled to a patient comprising: communicating a prescribed set of instructions to be accomplished over a predetermined period of time to a patient device to achieve alignment of one or more bones by adjustment of the bone alignment device; receiving information from the patient device regarding one or more adjustments made to the bone alignment device; a step for analyzing the information received; a step for calculating a revised set of instructions to be accomplished over a predetermined period of time to achieve alignment of the one or more bones; and communicating the revised set of instructions to the patient device to enable a transformation of the bone alignment device in accordance with the revised set of instructions.

In one aspect of the invention, the method further comprises a step for adjusting the bone alignment device in accordance with the revised set of instructions.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the invention should not be limited by any of the above-described exemplary embodiments, but should be defined only in accordance with the claims and their equivalents.

The invention claimed is:

1. A computer-implemented method, comprising:
performing, using at least one processor, one or more adjustments in a plurality of adjustments to be performed to a bone alignment device using one or more instructions specified in a prescription for the bone alignment device, the bone alignment device being affixed to a patient;
receiving, using the at least one processor, data associated with the performed one or more adjustments, the data includes data resulting from monitoring, by the bone alignment device, of healing of one or more bones of the patient;
generating, using the at least one processor, a revised prescription for the bone alignment device based on the received data, the revised prescription including one or more revised instructions for one or more revised adjustments to the bone alignment device; and
causing, using the at least one processor, automatic execution of the one or more revised instructions to perform the one or more revised adjustments to the bone alignment device.

2. The method of claim 1, wherein the prescription is generated based on at least one of: a patient deformity measurement information, an initial frame configuration of the bone alignment device, a distraction rate, a correction rate, and any combination thereof.

3. The method of claim 1, wherein the prescription identifies one or more predetermined times at which to perform each of the one or more adjustments to the bone alignment device.

4. The method of claim 3, wherein the revised prescription identifies one or more revised predetermined times at which to perform each of the one or more revised adjustments to the bone alignment device.

5. The method of claim 1, wherein the prescription identifies a predetermined period of time during which the one or more adjustments to the bone alignment device are performed.

6. The method of claim 5, wherein the revised prescription identifies a revised predetermined period of time during which the one or more revised adjustments to the bone alignment device are performed.

7. The method of claim 6, wherein the revised predetermined period of time is greater than the predetermined period of time.

8. The method claim 1, wherein the received data includes one or more images of the bone alignment device after performing of the one or more adjustments.

9. The method of claim 8, wherein the revised prescription is generated based on the one or more images.

10. The method of claim 1, wherein the received data includes data associated with one or more sensed forces transmitted through one or more components of the bone alignment device.

11. The method of claim 1, wherein the generating comprises:
comparing, using the received data, the one or more adjustments performed to the bone alignment device with the plurality of adjustments to be performed to the bone alignment device; and identifying at least one of the plurality of adjustments to be performed to the bone alignment device that was not performed;

generating the revised prescription based on at least one of: the one or more adjustments performed to the bone alignment device, the plurality of adjustments to be performed to the bone alignment device, the at least one of the plurality of adjustments to be performed to the bone alignment device that were not performed, and any combination thereof.

12. The method of claim 1, wherein the received data includes an indication of a pain experienced by the patient, wherein the generating including generating the revised prescription based on at least one of: the one or more adjustments performed to the bone alignment device, the plurality of adjustments to be performed to the bone alignment device, the pain experienced by the patient, and any combination thereof.

13. The method of claim 12, wherein the received data indicates whether the pain experienced by the patient is greater than or equal to an excessive quantity of pain, wherein the generating including generating the revised prescription including a lower distraction rate for one or more struts of the bone alignment device based on a determination that the pain experienced by the patient is greater than or equal to the excessive quantity of pain.

14. The method of claim 1, wherein the generating comprises:
comparing, using the received data, the one or more adjustments performed to the bone alignment device with the plurality of adjustments to be performed to the bone alignment device;
identifying at least one of the one or more adjustments performed to the bone alignment device that is not within the plurality of adjustments to be performed to the bone alignment device; and
generating the revised prescription based on at least one of: the one or more adjustments performed to the bone alignment device, the plurality of adjustments to be performed to the bone alignment device, the at least one of the one or more of adjustments performed to the bone alignment device that is not within the plurality of adjustments to be performed to the bone alignment device, and any combination thereof.

15. At least one non-transitory computer-readable storage medium comprising instructions that when executed by at least one processor of at least one computing device, cause the at least one computing device to perform operations comprising:
performing one or more adjustments in a plurality of adjustments to be performed to a bone alignment device using one or more instructions specified in a prescription for the bone alignment device, the bone alignment device being affixed to a patient;
receiving data associated with the performed one or more adjustments, the data includes data resulting from monitoring, by the bone alignment device, of healing of one or more bones of the patient;
generating a revised prescription for the bone alignment device based on the received data, the revised prescription including one or more revised instructions for one or more revised adjustments to the bone alignment device; and
causing automatic execution of the one or more revised instructions to perform the one or more revised adjustments to the bone alignment device.

16. The non-transitory computer-readable storage medium of claim 15, wherein the prescription is generated based on at least one of: a patient deformity measurement information, an initial frame configuration of the bone alignment device, a distraction rate, a correction rate, and any combination thereof.

17. The non-transitory computer-readable storage medium of claim 15, wherein the prescription identifies one or more predetermined times at which to perform each of the one or more adjustments to the bone alignment device, wherein the revised prescription identifies one or more revised predetermined times at which to perform each of the one or more revised adjustments to the bone alignment device.

18. The non-transitory computer-readable storage medium of claim 15, wherein the prescription identifies a predetermined period of time during which the one or more adjustments to the bone alignment device are performed, wherein the revised prescription identifies a revised predetermined period of time during which the one or more revised adjustments to the bone alignment device are performed, the revised predetermined period of time being greater than the predetermined period of time.

19. The non-transitory computer-readable storage medium claim 15, wherein the received data includes one or more images of the bone alignment device after performing of the one or more adjustments, wherein the revised prescription is generated based on the one or more images.

20. A system, comprising:
at least one processor; and
at least one non-transitory storage media storing instructions, that when executed by the at least one processor, cause the at least one processor to perform operations including
performing one or more adjustments in a plurality of adjustments to be performed to a bone alignment device using one or more instructions specified in a prescription for the bone alignment device, the bone alignment device being affixed to a patient;
receiving data associated with the performed one or more adjustments, the data includes data resulting from monitoring, by the bone alignment device, of healing of one or more bones of the patient;
generating a revised prescription for the bone alignment device based on the received data, the revised prescription including one or more revised instructions for one or more revised adjustments to the bone alignment device; and
causing automatic execution of the one or more revised instructions to perform the one or more revised adjustments to the bone alignment device.

21. The method of claim 1, wherein the data resulting from monitoring of healing includes force data sensed by the bone alignment device.

* * * * *